(12) United States Patent
Larsen

(10) Patent No.: US 7,794,393 B2
(45) Date of Patent: Sep. 14, 2010

(54) RESECTOSCOPIC DEVICE AND METHOD

(76) Inventor: Dane M. Larsen, 46 Melody La., Plattsburgh, NY (US) 12901

( * ) Notice: Subject to any disclaimer, the term of this patent is extended or adjusted under 35 U.S.C. 154(b) by 1189 days.

(21) Appl. No.: 11/279,665

(22) Filed: Apr. 13, 2006

(65) Prior Publication Data

US 2007/0244353 A1    Oct. 18, 2007

(51) Int. Cl.
  *A61B 1/12*  (2006.01)
(52) U.S. Cl. .................. 600/159; 600/105; 606/46
(58) Field of Classification Search ........... 600/105, 600/156, 158–159; 606/46–47, 45
  See application file for complete search history.

(56) References Cited

U.S. PATENT DOCUMENTS

| | | |
|---|---|---|
| 1,127,948 A | 2/1915 | Wappler |
| 1,303,135 A | 5/1919 | Wappler |
| 1,609,014 A | 11/1926 | Dowd |
| 1,615,494 A | 1/1927 | Waring |
| 1,930,214 A | 10/1933 | Wappler |
| 1,931,740 A | 10/1933 | Ryan |
| 2,012,363 A | 8/1935 | Vogel |
| 2,484,059 A | 10/1949 | Wallace |
| 2,815,757 A | 12/1957 | Piar |
| 3,835,842 A | 9/1974 | Iglesias |
| 3,850,162 A | 11/1974 | Iglesias |
| 3,850,175 A * | 11/1974 | Iglesias ............ 606/46 |
| 3,939,839 A | 2/1976 | Curtiss |
| 3,942,530 A | 3/1976 | Northeved |
| 3,945,375 A | 3/1976 | Banko |
| 4,132,227 A | 1/1979 | Ibe |
| 4,362,160 A | 12/1982 | Hiltebrandt |
| 4,679,558 A | 7/1987 | Kensey et al. |
| 4,681,106 A | 7/1987 | Kensey et al. |

(Continued)

FOREIGN PATENT DOCUMENTS

EP    1310207 A2    5/2003

(Continued)

OTHER PUBLICATIONS

International Search Report for PCT/US07/66055, dated Apr. 14, 2008.

(Continued)

*Primary Examiner*—Linda C Dvorak
*Assistant Examiner*—Benjamin Lee
(74) *Attorney, Agent, or Firm*—Weitzman Law Offices, LLC

(57) ABSTRACT

A surgical instrument has a channel dimensioned to receive a viewing instrument and enable the viewing instrument to be moved to or from a position near an optically transparent portion of a blunt, enclosed distal end of a shaft to provide unobstructed viewing through the distal end, and a position to the proximal side of an enclosed working area to provide viewing of the enclosed working area. A surgical instrument also or alternatively has a fluid routing switch within a shaft which can selectively connect a fluid infusion channel to at least one fluid export pore or a return channel. A method involves moving a viewing instrument to or from a position near an optically transparent portion of a blunt, enclosed distal shaft end and a proximal side of an enclosed working area. A method also or alternatively involves changing a position of a fluid routing switch within the shaft.

26 Claims, 15 Drawing Sheets

U.S. PATENT DOCUMENTS

| | | | |
|---|---|---|---|
| 4,756,309 A | 7/1988 | Sachse et al. | |
| 4,815,462 A | 3/1989 | Clark | |
| 4,834,729 A | 5/1989 | Sjostrom | |
| 4,842,578 A | 6/1989 | Johnson et al. | |
| 4,890,602 A | 1/1990 | Hake | |
| 4,893,613 A | 1/1990 | Hake | |
| 4,922,902 A | 5/1990 | Wuchinich et al. | |
| 4,957,492 A | 9/1990 | McVay | |
| 4,986,825 A | 1/1991 | Bays et al. | |
| 4,998,527 A | 3/1991 | Meyer | |
| 5,007,908 A | 4/1991 | Rydell | |
| 5,019,036 A | 5/1991 | Stahl | |
| 5,047,027 A | 9/1991 | Rydell | |
| 5,092,872 A | 3/1992 | Segalowitz | |
| 5,127,393 A * | 7/1992 | McFarlin et al. | 600/114 |
| 5,133,713 A | 7/1992 | Huang et al. | |
| 5,169,397 A | 12/1992 | Sakashita et al. | |
| 5,176,677 A | 1/1993 | Wuchinich | |
| 5,201,731 A | 4/1993 | Hakky | |
| 5,267,998 A | 12/1993 | Hagen | |
| 5,269,780 A | 12/1993 | Roos | |
| 5,277,696 A | 1/1994 | Hagen | |
| 5,295,990 A | 3/1994 | Levin | |
| 5,304,124 A | 4/1994 | Essig et al. | |
| 5,312,399 A | 5/1994 | Hakky et al. | |
| 5,320,091 A | 6/1994 | Grossi et al. | |
| 5,320,627 A | 6/1994 | Sorensen et al. | |
| 5,325,860 A | 7/1994 | Seward et al. | |
| 5,335,663 A | 8/1994 | Oakley et al. | |
| 5,364,395 A | 11/1994 | West, Jr. | |
| 5,392,765 A | 2/1995 | Muller | |
| 5,403,276 A | 4/1995 | Schecter et al. | |
| 5,443,472 A | 8/1995 | Li | |
| 5,456,689 A | 10/1995 | Kresch et al. | |
| 5,549,541 A | 8/1996 | Muller | |
| 5,643,304 A | 7/1997 | Schechter et al. | |
| 5,681,262 A | 10/1997 | Isse | |
| 5,685,840 A | 11/1997 | Schechter et al. | |
| 5,730,752 A | 3/1998 | Alden et al. | |
| 5,800,362 A | 9/1998 | Kobren et al. | |
| 5,807,240 A | 9/1998 | Muller et al. | |
| 5,810,809 A | 9/1998 | Rydell | |
| 5,814,044 A | 9/1998 | Hooven | |
| 5,904,681 A | 5/1999 | West, Jr. | |
| 5,989,264 A | 11/1999 | Wright | |
| 5,993,445 A | 11/1999 | Issa | |
| 6,032,673 A | 3/2000 | Savage et al. | |
| 6,083,177 A | 7/2000 | Kobren et al. | |
| 6,090,103 A | 7/2000 | Hakky et al. | |
| 6,117,133 A | 9/2000 | Zappala | |
| 6,132,428 A | 10/2000 | VanDusseldorp | |
| 6,214,001 B1 | 4/2001 | Casscells et al. | |
| 6,346,107 B1 | 2/2002 | Cucin | |
| 6,400,980 B1 * | 6/2002 | Lemelson | 600/478 |
| 6,500,113 B2 | 12/2002 | Vilos | |
| 6,537,273 B1 | 3/2003 | Sosiak et al. | |
| 6,589,237 B2 | 7/2003 | Woloszko et al. | |
| 6,663,628 B2 | 12/2003 | Peters | |
| 6,676,658 B2 | 1/2004 | Burbank et al. | |
| 6,726,684 B1 | 4/2004 | Woloszko et al. | |
| 6,746,395 B2 | 6/2004 | Brommersma et al. | |
| 6,872,207 B2 | 3/2005 | Ohyarna et al. | |
| 6,896,674 B1 | 5/2005 | Woloszko et al. | |
| 6,918,880 B2 | 7/2005 | Brookner et al. | |
| 6,949,096 B2 | 9/2005 | Davison et al. | |
| 6,971,989 B2 | 12/2005 | Yossepowitch | |
| 6,997,934 B2 | 2/2006 | Snow et al. | |
| 2001/0018550 A1 | 8/2001 | Boebel et al. | |
| 2003/0181906 A1 * | 9/2003 | Boebel et al. | 606/46 |
| 2004/0242959 A1 | 12/2004 | Nosel | |
| 2005/0049459 A1 | 3/2005 | Hern | |
| 2005/0070893 A1 | 3/2005 | Aue et al. | |
| 2005/0165272 A1 | 7/2005 | Okada et al. | |
| 2006/0009761 A1 | 1/2006 | Aue et al. | |
| 2006/0015007 A1 | 1/2006 | Aue et al. | |

FOREIGN PATENT DOCUMENTS

| | | |
|---|---|---|
| GB | 2 408 688 | 6/2005 |
| WO | WO 9911184 | 3/1999 |
| WO | WO 03/065908 A1 | 8/2003 |
| WO | WO 2004 032732 | 4/2004 |
| WO | WO 2005 009213 | 2/2005 |
| WO | WO 2005 086683 | 9/2005 |
| WO | WO 2005 104966 | 11/2005 |
| WO | WO 2006/021880 | 3/2006 |

OTHER PUBLICATIONS

Carter, James E. and McCarus, Steven, D., "Laparoscopic Myomectomy, Time and Cost Analysis of Power vs. Manual Morcellation," *Journal of Reproductive Medicine*, vol. 42, No. 7, pp. 383-388, Jul. 1997.

Carter, James E. and McCarus, Steven D., "Time Savings Using the Steiner Morcellator in Laparoscopic Myomectomy," Selected Scientific Abstracts, *Wey Memorial Library*, Lemira, New York, 1 page.

Carter, J.E. et al., "Laparoscopic Outpatient Treatment of Large Myomas," Selected Scientific Abstracts, *Wey Memorial Library*, Lemira, New York, 1 page.

Miller, Charles Edward, "Methods of tissue extraction in advanced laparoscopy," *Current Opinion in Obstetrics and Gynecology*, vol. 13, pp. 399-405, 2001.

Murakami, Takashi et al., "Safe techniques in surgery for hysteroscopic myomectomy," *J. Obstet. Gynaecol. Res.* vol. 31, No. 3, pp. 216-223, Jun. 2005.

Carter, James E. and McCarus, Steven D., "Time Savings Using the Steiner Morcellator in Laparoscopic Myomectomy," Selected Scientific Abstracts, *Wey Memorial Library*, Lemira, New York, 1 page, 1996.

Carter, J.E. et al., "Laparoscopic Outpatient Treatment of Large Myomas," Selected Scientific Abstracts, *Wey Memorial Library*, Lemira, New York, 1 page, 1996.

Supplementary European Search Report (dated Dec. 11, 2009) for cooresponding European Patent Application No. EP07760180.

* cited by examiner

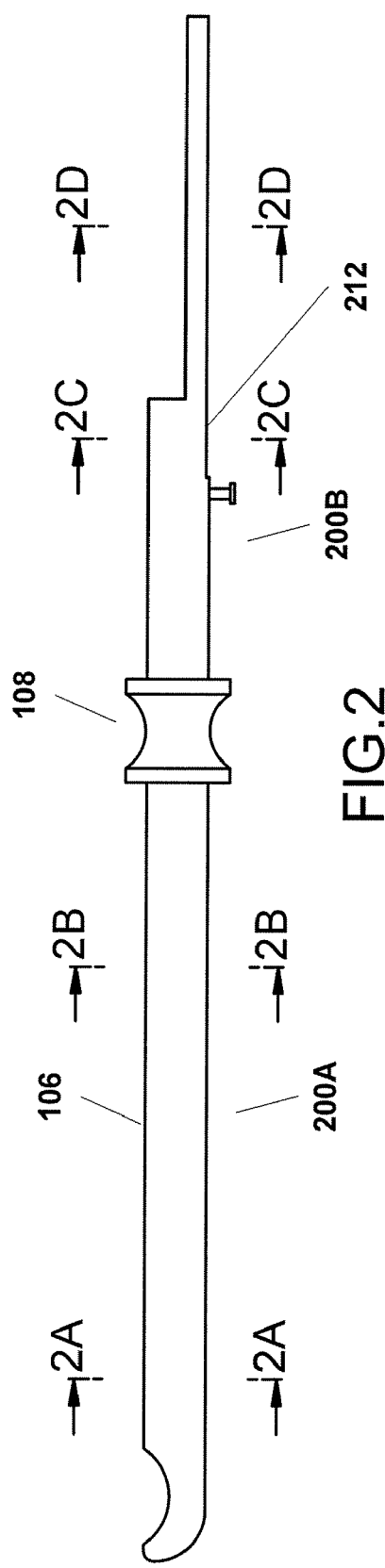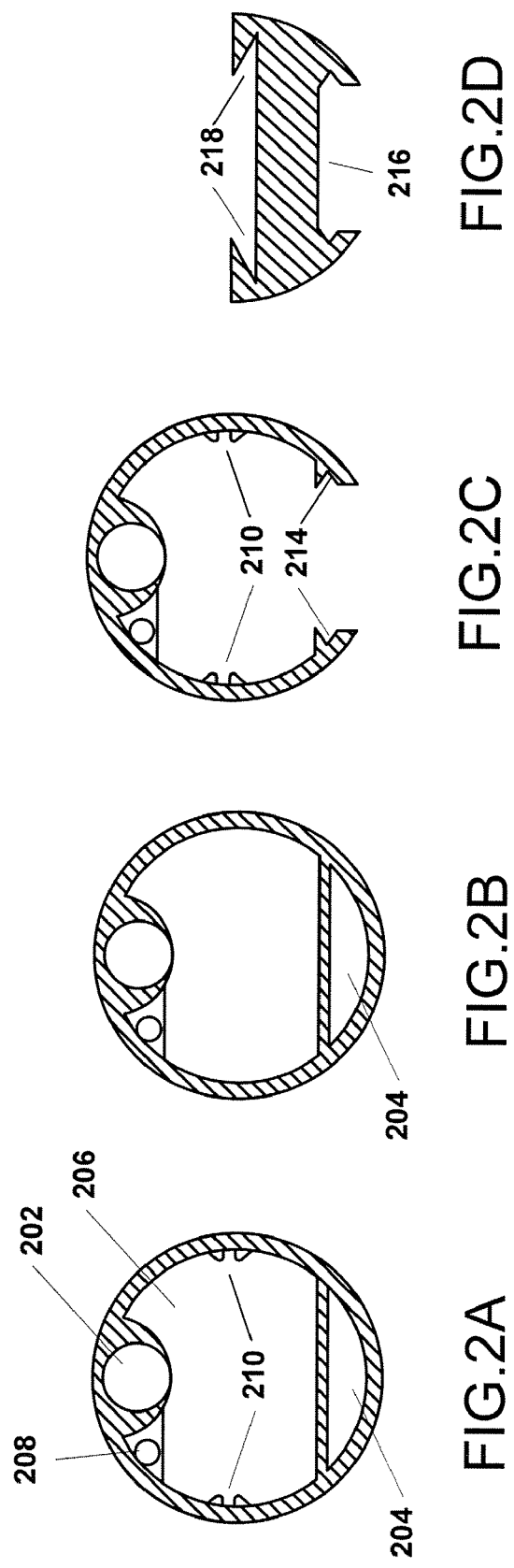

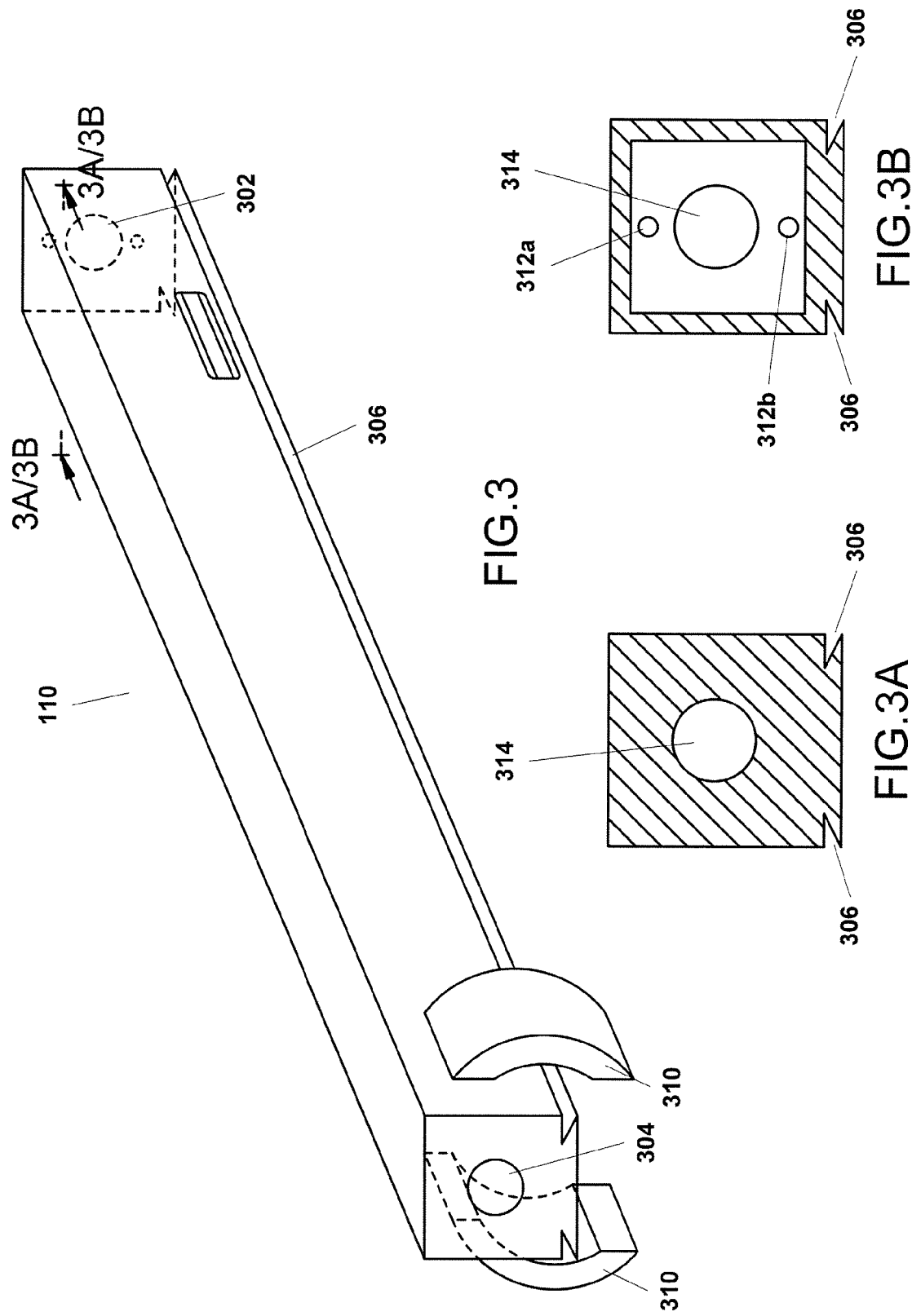

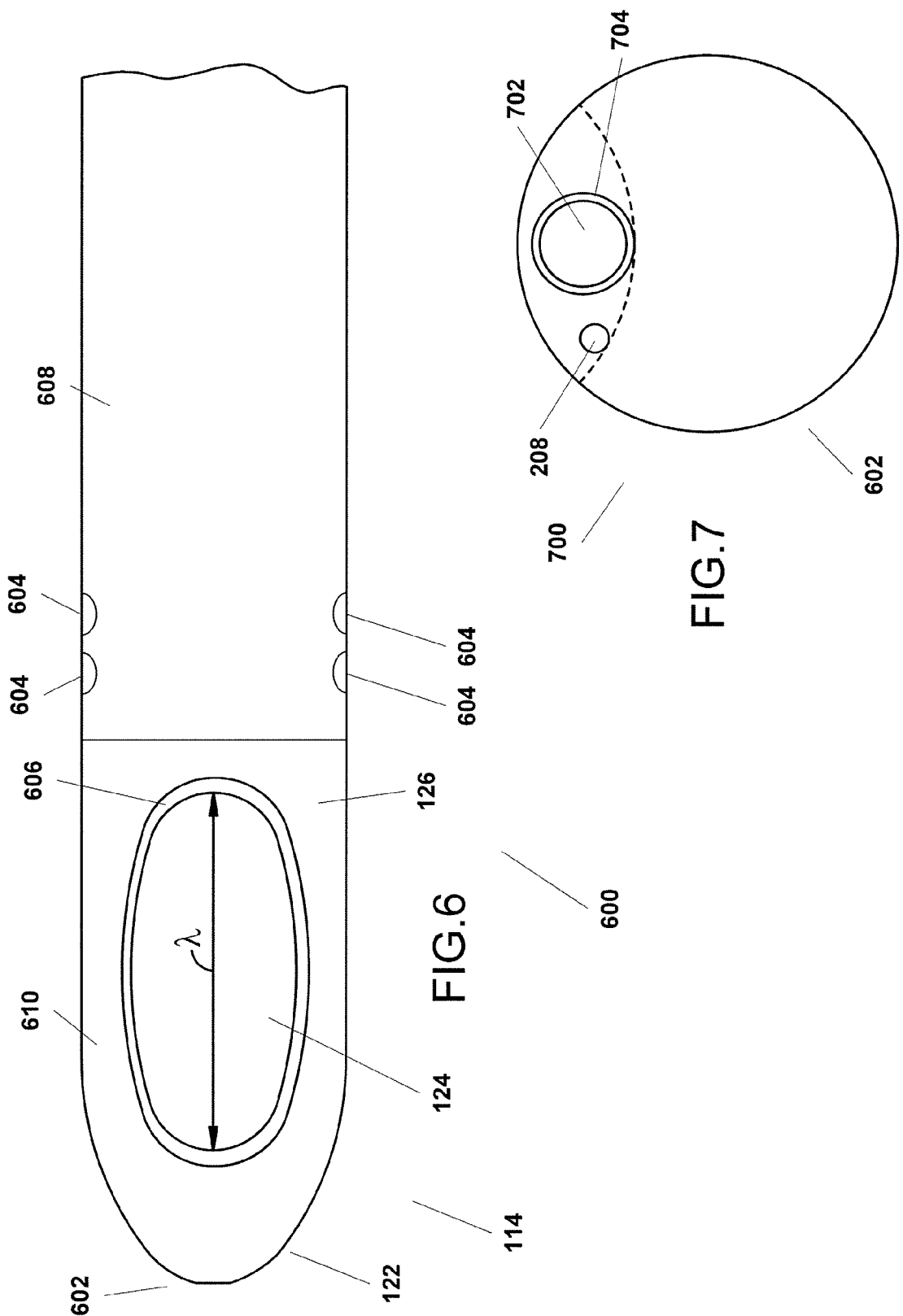

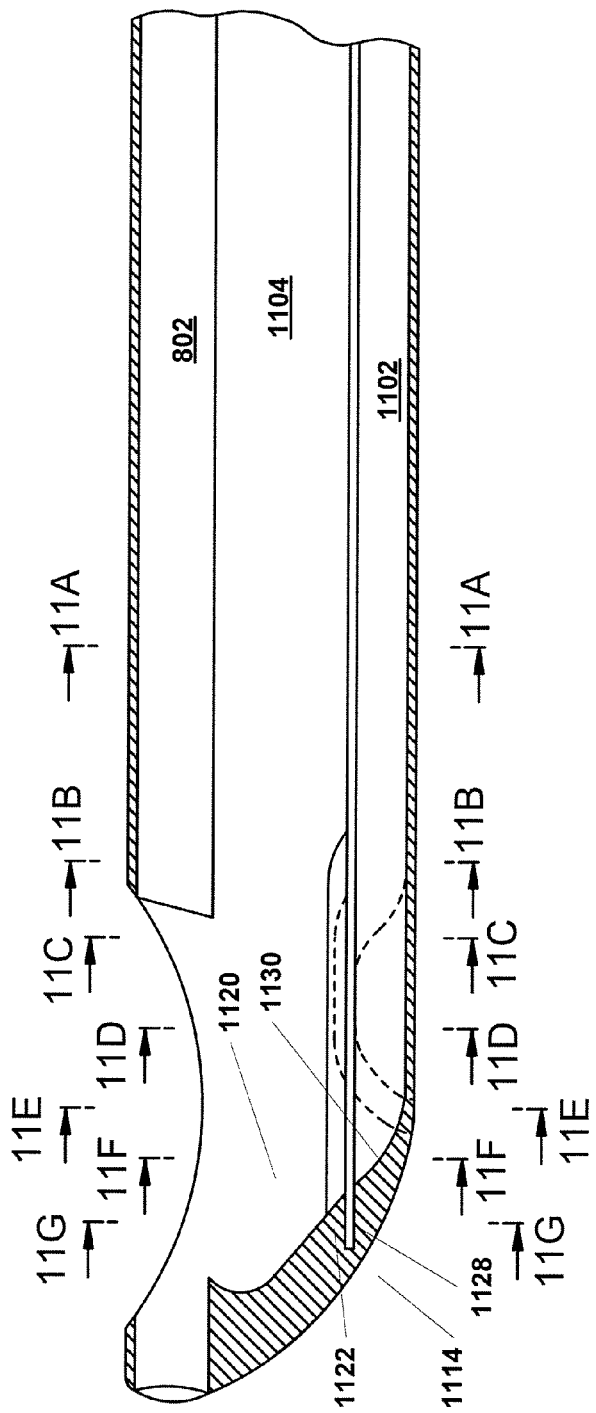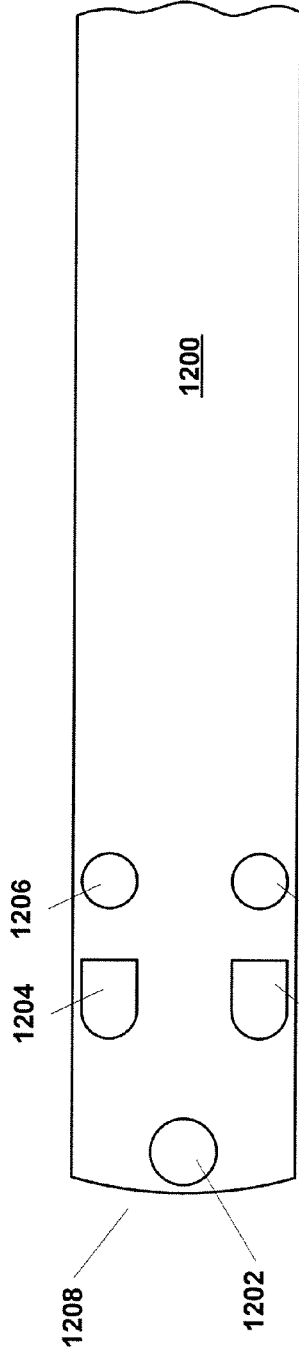
FIG. 11
FIG. 12

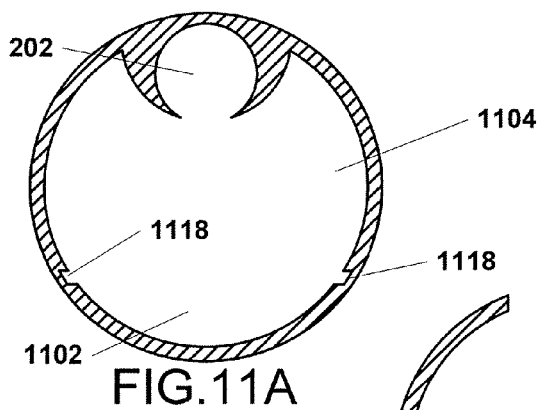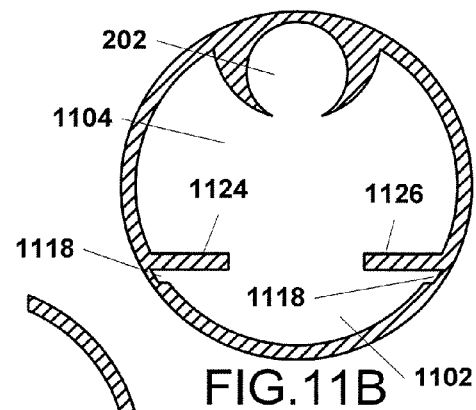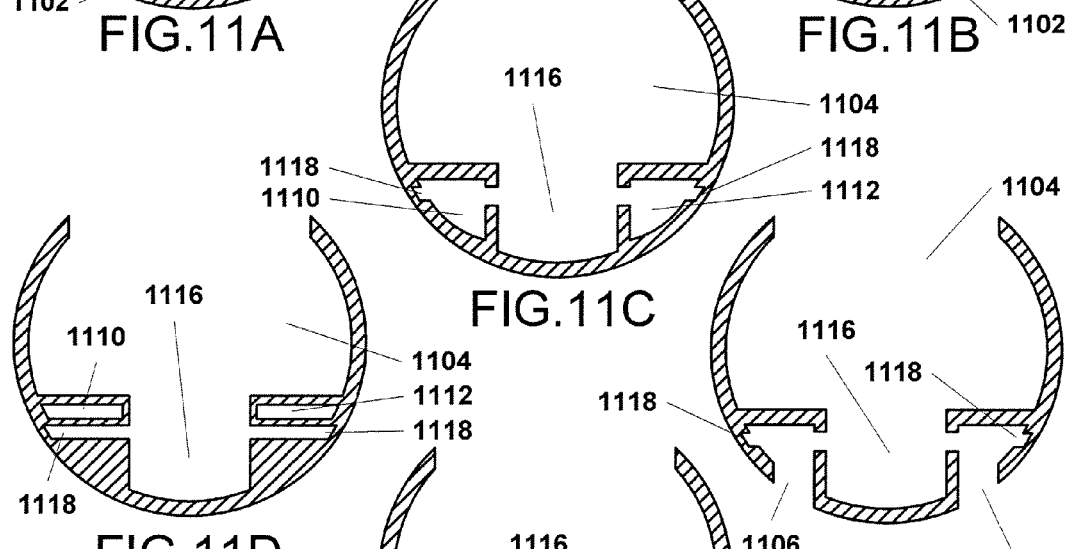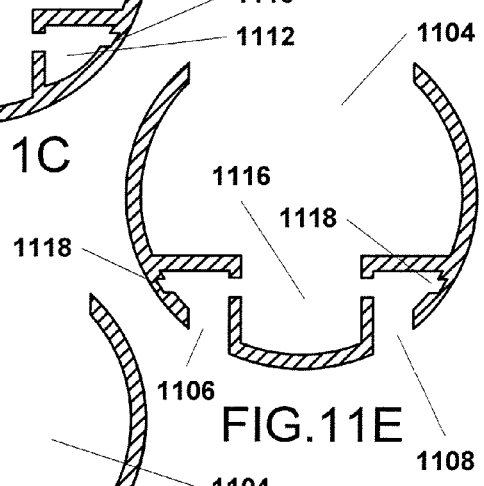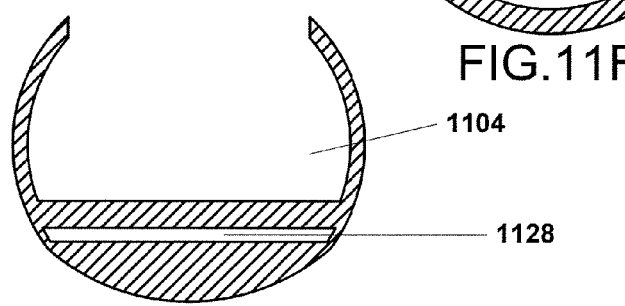

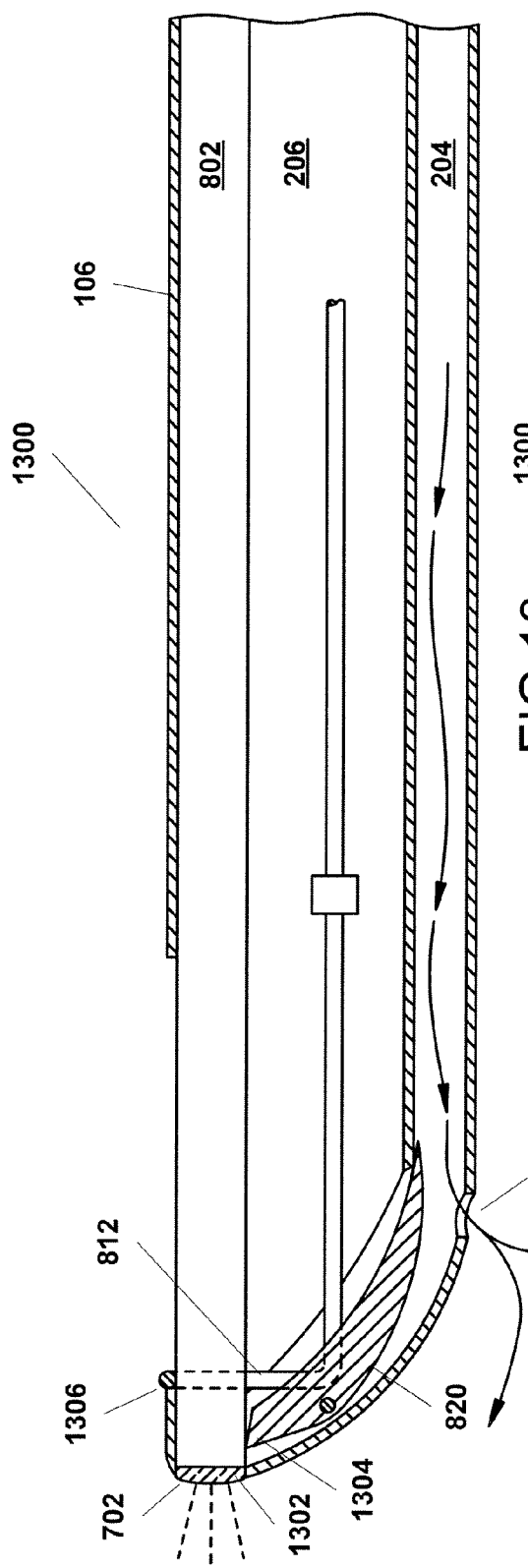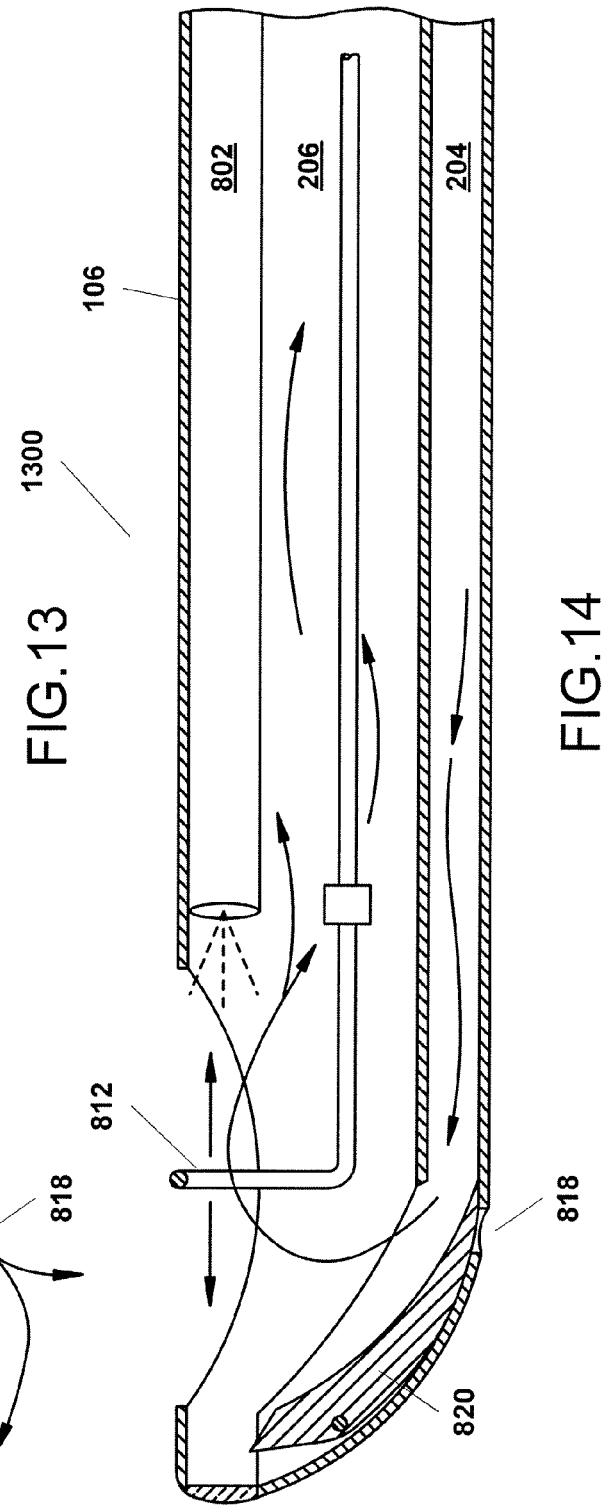
FIG. 13
FIG. 14

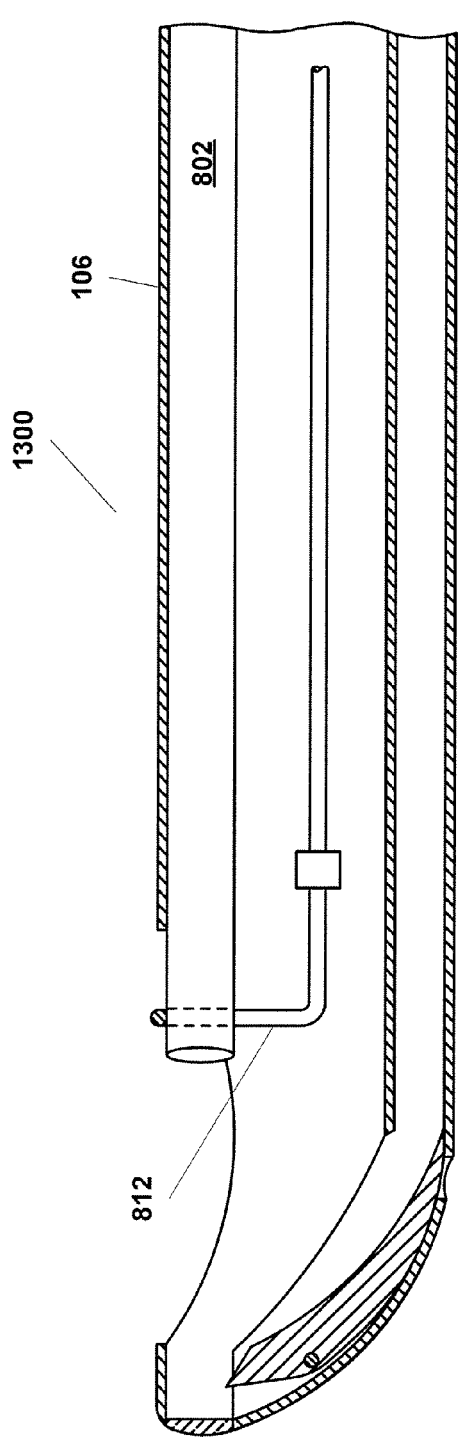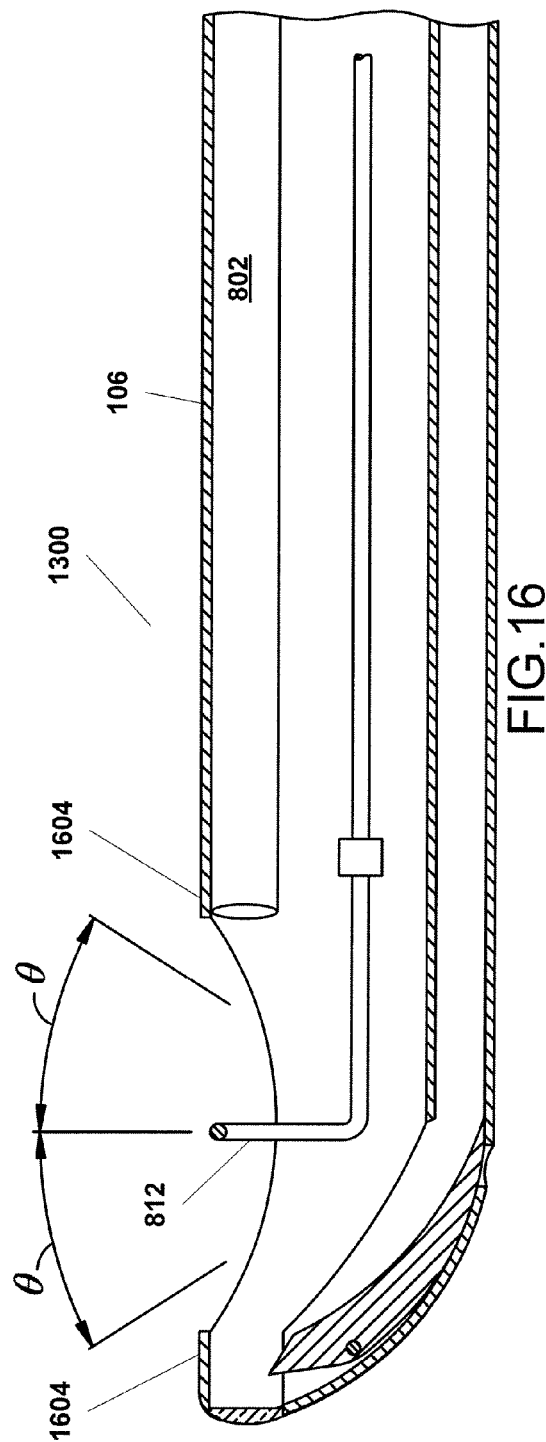

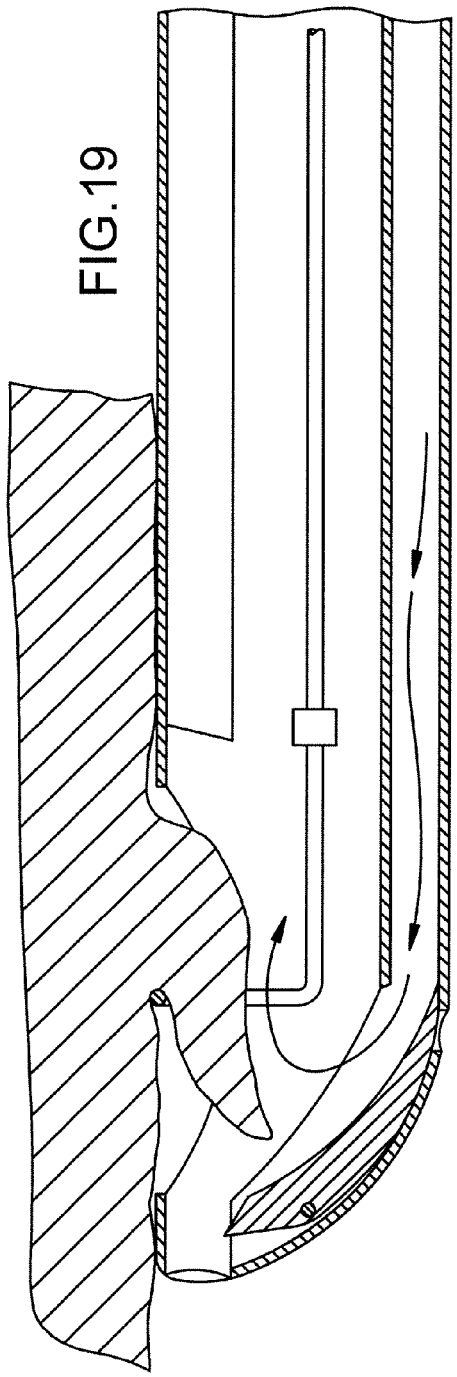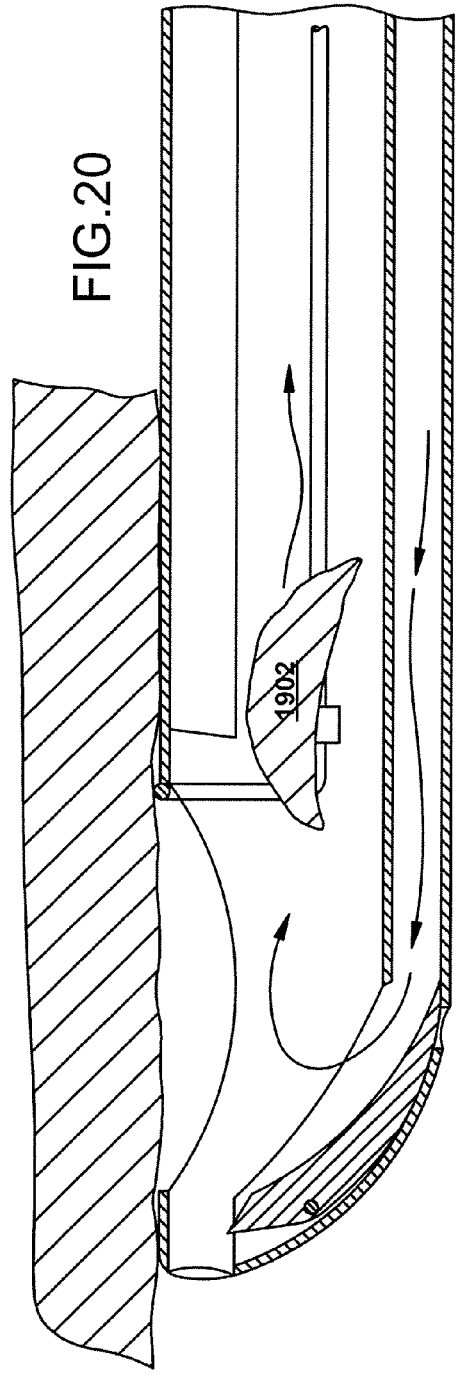

RESECTOSCOPIC DEVICE AND METHOD

FIELD OF THE INVENTION

The present invention relates to surgical devices and, more particularly, to surgical devices used for resection of tissue from within a body cavity.

BACKGROUND TO THE INVENTION

In surgical operations it is often necessary to insert tubular instruments into small body cavities in order to manipulate, modify or resect pathological tissues which may include, for example, lesions, polyps, cysts, fibroids, lymph nodes, choroid tissues, and other abnormal tissue growths, to name a few. When an instrument is introduced into a body cavity during an operative procedure, in some cases, undesired tissue injury can be expected. However, the risk of significant undesired tissue injury increases as the ability to view what is happening with the instrument decreases. In other words, there is significantly greater risk of injury when an instrument must be inserted and used "blindly" (i.e. only by feel) than there is when the insertion path and area of use can be fully viewed.

While, in some cases, a potential undesirable injury such as a laceration or perforation may not present a significant risk so as to require remedial action (i.e. it will heal on its own), in other cases, such as an injury occurring in an organ like the uterus, intestine or bowel, a laceration or perforation can be life threatening—in the former organ due to excessive bleeding and, in the latter organs, by potentially causing peritonitis.

In general, the evolution of endoscopic surgical technology has vastly reduced average morbidities for many operative procedures, and methods for resection of pathological tissue have improved over time. However, despite these advances organ lacerations and perforations still occur. Moreover, currently available technologies are designed to promote freedom to the surgeon through a largely exposed cutting member and thus increase, rather than decrease the possibility of causing undesirable tissue injury. In addition, current resectoscopic instruments are generally complicated, balky, and often require multi-component reconfiguration during use.

When tissue is removed during a surgical procedure, capture of the resected tissue is necessary for surgical pathology testing. Unfortunately, in certain organs, efficient removal of pathological tissue from an operative site remains problematic. For example, with respect to removal of pathological tissue from the uterus, the present practice for hysteroscopy follows a process beset by multiple task interruptions. The process begins with the trays containing the hysteroscope and resectosocopic instruments opened onto the sterile field for assembly into one of two separate operational modes.

First, a diagnostic sleeve is usually set up for use with the hysteroscope to allow the surgeon entry into the uterus. The surgeon performs an initial diagnostic hysteroscopy to identify the tissue(s) to be removed and their location.

After the diagnostic hysteroscopy, the setup is withdrawn and disassembled with the scope extracted from the assembly. A separate resectoscopic instrument is then assembled involving placement and alignment of an electrode upon the scope including electrode insertion and fixation into a small hole. A bridge piece is then inserted onto the assembly along with a new sleeve assembly. A fluid pressure regulator is attached to the inflow port of the instrument and a power source is connected.

Now the resectoscopic instrument is carefully entered into the uterus after further dilation of the cervix to accommodate its larger diameter and pipe-like tip. Here the surgeon must be very careful to avoid perforation of the uterus by the cutting tendency of the resectoscope itself. In addition, the surgeon must avoid accumulation of endometrium tissues within the tip assembly since those tissues will obscure the view. If the view becomes too obscured, removal and cleaning prior to reinsertion is required.

Once the resectoscope is within the uterine cavity, the surgeon employs careful adjustment between the inflow and outflow valves to infuse fluid into the uterus to open it and to remove fluid within the uterus which has become tainted with blood from the abrasion of tissues that is inherent with the insertion. Only when a balance between the inflow and outflow is obtained such that where the uterus is opened and inflated and the view is clear can the actual resection work begin. A typical balanced flow rate is around 10 cc/min.

The resectoscope is then maneuvered into position near the tissue to be resected and, with a clear view for resection, the loop electrode is extended beyond the distal end of the resectoscope. The loop is then placed near the tissue to be resected, the electroloop is activated, and the loop is drawn back toward the resectoscope itself causing the loop to simultaneously cut off a piece of the tissue and cauterize the wound in the tissue left behind. The process of extension and withdrawal would then be repeated until the full extent of the identified tissue is removed. However, the process is rarely that straightforward. More typically, the resection process is repeatedly interrupted by clogging of the tip assembly by tissue, or by sticking of the tissue to the loop itself. When this happens, removal, cleaning and reinsertion of the entire assembly may be necessary.

In addition, as noted above, each tissue piece must be captured for surgical pathology. With the present devices, the resectoscope can be employed to intentionally snare and remove each tissue piece, but this requires removal of the entire assembly to remove the individual tissue piece, re-insertion of the resectoscope, abatement of any new bleeding, re-attaining of the proper the balance between fluid infusion and removal to gain an adequate view, and only then, working on the next small tissue piece to be resected. Alternatively, if the resectoscope is not used, a tissue forcep may be blindly substituted for the resectoscope in order to attempt removal of the tissue. In either case, diagnostically important pieces of tissue may be lost in the effluvium of uterine deflation, or dropped and lost in the handoff from surgeon to technician.

Still further, if cautery needs exceed the ability of the resection loop during the process, the entire mechanism must be withdrawn and disassembled to remove the electro-loop and substitute a roller-ball electrode. Then, re-assembly, and subsequent re-insertion and fluid flow re-balancing are required in order to accomplish this phase of cautery. Then, if further resection is still necessary or desired after the cautery, the removal, reconfiguration, re-balancing, etc. process must be repeated.

Once the procedure is finally complete from the surgeons perspective, the process must continue for purposes of surgical pathology. In that regard, the instrument is handed off to a technician who disassembles it and removes any tissue pieces that have attached to any of the multiple sleeves, auxiliary instruments, obturators, stop-cocks, scope, bridge pieces, holes and grooves. In addition, the electroloop is removed and disposed of into the sharps container.

Since the instruments are all reused, after disassembly, the multiple elements must be transported to the area where final cleaning is done before sterilization and re-packaging. Thereafter, at some point a transport is required to return the now cleaned, sterilized and repacked unassembled kit and tray to the peri-operative supply area for its next use.

Some newer systems employ variations on the same basic free-flow hysteroscopic resectoscope in which an auxiliary instrument can be inserted through the hysteroscope for the purpose of tissue capture and removal.

In some variants tissue morcellation is employed which requires time. Other variants require a complex opening mechanism to obliquely pass a small auxiliary tissue cutting and capture instrument to thereby allow for tissue capture and removal. These geometric changes increase the size of the instrument and thus limit the use of the instrument to areas of the body or body cavity that can accommodate the size change and/or overall increased size. These methods also involve optically guided capture and manipulation of tissue morsels in order to accomplish their export with or without further morcellation. Most of these variant methods require interruption of cutting to allow for removal of resected tissue. In addition, none of these variant techniques meaningfully reduce organ perforation risk. Still further, to avoid removal of an excessive amount of tissue, resection is typically done in a series of passes, with every pass involving a "guess" as to the required (and actual) depth of cut, particularly because gasses from tissue destruction and heat largely obscure the cutting loop from precise view during the actual cutting. As a result, surgeons are forced to weigh and ultimately succumb to the trade-off between over-removal with its attendant risk of organ perforation or under-removal with the prospect that a repeat procedure may, at some point, be necessary.

Removal of pathological tissue from other organs routinely involves, to varying degrees, multiple steps of a somewhat analogous nature (i.e. multiple insertions/removals and issues relating to capture of resected pathological tissue) and thus analogous or similar problems exist with those operations as well.

As will be appreciated, the above example procedure to remove pathological tissue from the uterus is time consuming and typically takes between 30 and 60 minutes to perform. With operating room costs exceeding several thousand dollars an hour, this can lead to substantial costs for a patient as well as the hospital in which the resection is performed.

Thus, there is a need for a surgical device that does not suffer from problems attendant with existing devices.

In addition, there is a need for a surgical device that can reduce the time required to perform a resection procedure and thereby, the costs associated with doing so.

SUMMARY OF THE INVENTION

I have devised an instrument that can be used for resection of lesions or tissue that significantly reduces the above problems.

One example aspect involves a surgical instrument including a shaft having a proximal end and a blunt, enclosed distal end, the blunt, enclosed distal end being optically transparent over at least a portion of its area, a scope having a viewing end that is moveable within the shaft between a first position and a second position such that when in the first position within the shaft, the viewing end will be on a distal side of a working area within which resection can occur and proximate to the optically transparent portion of the distal end and provide an unobstructed view external to the blunt, enclosed distal end and when in the second position within the shaft, the viewing end will be on a proximal side of the working area and provide a view of the working area.

An alternative aspect involves a surgical instrument having a longitudinal shaft including an enclosed, blunt distal tip, an internal fluid flow path and an externalizable fluid flow path. The longitudinal shaft also has a working area defined by an opening in a side of the longitudinal shaft, located within the internal fluid flow path, and a switch, coupled to the internal fluid flow path and the externalizable fluid flow path which will control infusion fluid flow into the internal fluid flow path and the externalizable fluid flow path.

Another alternative aspect involves a method made up of: viewing insertion of a shaft, having a blunt, enclosed distal end, into a body cavity through the blunt distal end via an optical element located proximate to the distal end; causing a fluid flowing along the shaft from a proximal end to a distal end to exit the shaft through at least one export pore; changing a switch setting such that the fluid flowing in the proximal to distal direction will bypass a working area and, once past the working area will flow in the distal to proximal direction and pass through the working area; and causing a discrete piece of tissue to enter the working area so that it will be conveyed in the distal to proximal direction by the flow of the fluid.

Various implementations of my invention can provide one or more of the following advantages: fully integrated functionality, reduction in trauma from insertion, reduction in time to perform a resection procedure, accurate targeting of tissue to be resected, automatic limiting of cutting depth, and/or capture and export of all resected tissue and debris. Moreover, certain implementations can be disposable, in whole or part, resulting in cost savings due to avoidance of cleaning and re-sterilization issues.

Variants of the invention are suitable for use in, among others, gynecological, urological, proctological, thoracic, neurological, pulmenological, otolaryngological, gastrointestinal and laparoscopic procedures as well as other procedures in which a minimally invasive and minimally traumatic tissue resection is necessary or desirable.

Variants implementing the invention provide a further pathological benefit not available with current resection tools like macerators, morcellators and electrosurgical loops or knives. One problem with macerators and micro-morcellators is that they destroy large amounts of tissue, rendering them less suitable for pathological examination. Electrosurgical loops or knives that cauterize as they cut create a zone of tissue destruction on the edges of each side of the cut that is typically about 10 microns deep. While this zone is considered pathologically acceptable, it nevertheless represents a zone of pathological uncertainty. Advantageously, with variants that implement the invention, the size of the resected tissue pieces can be larger than with currently available devices resulting in a greater ratio of undamaged to destroyed tissue and, consequently, a larger volume of pathologically examinable tissue.

Moreover, the protected nature of the cutting part of the device reduces or eliminates the risk of organ perforation, allowing for performing bi-directional resection—in contrast to the way surgeons are taught to perform resections with conventional instruments.

In addition, different variants can provide one or more of the following further advantages: quick functional change among operational modes (i.e. inflation, viewing, resection, irrigation, etc.); true dual conformation with immediate re-conformation; single hand manipulation and control; fluid switching and internalization with vacuum actuated flow boosting for accelerated tissue export; automatic transfer and capture of resected tissue; intrinsic depth of cut control; elimination of separate and discrete insertion or extraction of obturators, tissue choppers; elimination or reduction in the use of accessory instruments or undertaking cycles of insertion, cavity infusion, target acquisition, withdrawal, disassembly, reassembly, reinsertion, subsequent cavity reinfusion & target reacquisition, etc. saving effort, time and, consequently, money; unobstructed panoramic diagnostic viewing pre and post-resection; a protected resection mechanism; minimally traumatic instrument insertion and manipulation; and inhibition or prevention of organ perforation by an activated electrode under proper use.

The advantages and features described herein are a few of the many advantages and features available from representative embodiments and are presented only to assist in understanding the invention. It should be understood that they are not to be considered limitations on the invention as defined by the claims, or limitations on equivalents to the claims. For instance, some of these advantages are mutually contradictory, in that they cannot be simultaneously present in a single embodiment. Similarly, some advantages are applicable to one aspect of the invention, and inapplicable to others. Thus, this summary of features and advantages should not be considered dispositive in determining equivalence. Additional features and advantages of the invention will become apparent in the following description, from the drawings, and from the claims.

BRIEF DESCRIPTION OF THE DRAWINGS

FIG. 2 is a simplified view of the shaft component of the resectoscope of FIG. 1;

FIG. 3 illustrates, in simplified form, the trolley mechanism for the variant of FIG. 1;

FIG. 6 illustrates, in simplified form, a top view of a portion of the distal end of the shaft;

FIG. 7 illustrates, in simplified form, an external end view of the blunt distal end portion of the shaft;

FIG. 11 illustrates, in simplified form, a longitudinal, cross sectional side-view of a further alternative shaft portion;

FIG. 12 illustrates, in simplified form, an example sliding control reed configured for use in conjunction with the shaft portion of FIG. 10;

FIG. 13 illustrates, in simplified form, the portion of the resectoscope of FIG. 8 as it would look during insertion;

FIG. 14 illustrates, in simplified form, the portion of the resectoscope of FIG. 8 as it would look during the "working" or resection process;

FIG. 15 illustrates, in simplified form, the portion of the resectoscope of FIG. 8 with the telescope or viewing apparatus moved ahead of the cutting member;

FIG. 16 illustrates, in simplified form, the portion of the resectoscope of FIG. 8 in an optional third configuration; and FIGS. 17-20 illustrate, in simplified form, different stages of tissue resection using the resectoscope.

DETAILED DESCRIPTION

Figure 1:
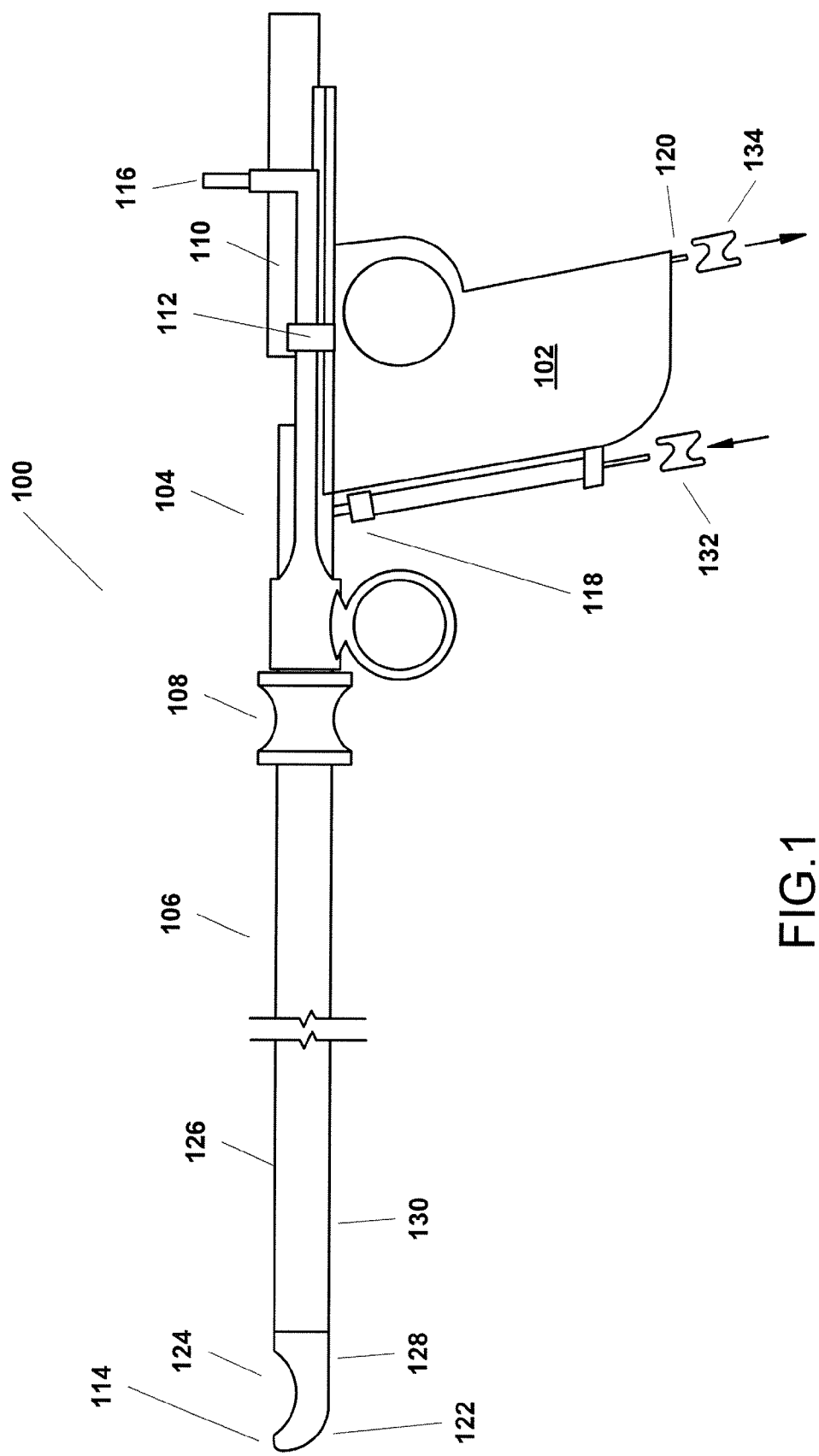
FIG. 1 is a simplified side view of one example variant of a resectoscope incorporating the present invention.

FIG. 1 is a simplified side view of one example variant of a resectoscope 100 incorporating the present invention. As shown in FIG. 1, this example resectoscope 100 is, in summary overview, made up of a partially hollowed out handle 102 and a control mechanism 104, both of which will be described in greater detail below, a shaft 106 connected at its proximal end to the handle 102, a port through which a telescope or other viewing apparatus, which may or may not involve use of fiber optic technology can be inserted (not shown), and a finger grip 108 on the shaft 106. The resectoscope 100 further includes a trolley mechanism 110 that facilitates movement of the telescope or other viewing apparatus that is contained within the shaft, a stop 112 that acts as a handle to allow manipulation of the trolley 110 and also limits movement of the trolley 110 mechanism towards the distal end 114 of the shaft, a power connector 116, a fluid inlet 118 and a vacuum port/fluid outlet 120. As can be seen in FIG. 1, the tip 122 of the shaft 106 at the distal end 114 is formed so as to have a physically closed blunt shape to dramatically reduce, if not eliminate, puncture or laceration risk. In addition, the shaft includes an opening or resection port 124 located on a side surface 126 of the shaft 106 near the distal tip 122.

Depending upon the particular implementation and intended use, the length of the shaft 106 can be anywhere from relatively short, for example (i.e. a few centimeters or less) where a shallow body cavity is involved, relatively long (i.e. in excess of 40 centimeters) where long cavities like the bowel or intestines are the intended application, or lengths in between, for applications such as intrauterine resection. Similarly, depending upon the particular implementation and intended use, the shaft can be rigid along its entire length, flexible along a portion of its length, or configured for flexure at only certain specified locations.

Still further, in some implementation variants, the shaft can be made up of two or more detachably interlocking segments 128, 130 for purposes of modularization.

The fluid inlet 118 is configured for connection to an adjustable pressure fluid infusion line via a stopcock 132 or other appropriate valve and, in most cases, also having a parallel free flow one way fluid reservoir to accommodate vacuum boosting.

The vacuum port/fluid outlet 120 is configured for attachment to, for example, a foot-pedal actuated boosted vacuum source via a stopcock 134 or other appropriate valve.

FIG. 2 is a simplified view of an example shaft 106 component suitable for use as part of the resectoscope of FIG. 1 and further includes cross sectional slices 2A through 2D taken at the points indicated to illustrate various features of this example implementation. Moreover, and advantageously, in some variants, the shaft 106 itself is separable from the non-handle components that make up the body of the resectoscope 100, for example as in FIG. 2, and in some cases, made up of two or more discrete modules. Some shaft variants are also disposable, whereas others can be sterilized for reuse. In general, the shaft 106 is formed as a hollowed multi-channel shaft or cannula, the details of which are explained with reference to the cross sectional slices of the shaft shown in FIGS. 2A through 2D taken at 2A-2A, 2B-2B, 2C-2C and 2D-2D. However, it should be understood that the cross sectional shapes are simply for illustrative purposes, the particular cross sectional shape being more relevant to the particular application for which the resectoscope will be used than to the invention.

Referring now to the cross sectional slice of FIG. 2A taken at 2A-2A, this variant of resectoscope shaft 106 incorporates a channel or portal for a telescope or other viewing apparatus 202, a fluid infusion channel 204 through which fluid can be infused from the proximal end towards the distal end, a capture or return channel 206 through which fluid and resected tissue morsels are conveyed from the distal to the proximal end, one or more optional auxiliary channels 208 or other arrangement of appropriate size extending to at least the working area and, if desired, to the distal tip itself to allow for, for example: further connections to be made; objects, for example, catheters, drains, ureteral stents or tubal occlusion devices to be inserted; to provide a brief flow of liquid nitrogen or other cryo-cautery fluid to accomplish hemostasis; allow for passage of an auxiliary cauterization element to perform conventional cautery; or allow for a stylet to be passed to the vicinity of the working area or beyond the distal tip. In addition, in this variant, the shaft 106 is of a different modular configuration from that of FIG. 1, with the grip 108 of this variant being used as a coupler to couple a main portion 200A of the shaft from a proximal portion 200B. The shaft 106 also optionally includes a pair of guides 210 that limit the cutting member in this variant to longitudinal movement. In this illustrated variant, the guides are configured for when an electrosurgical wire loop is illustratively used (not shown in this FIG.).

The cross sectional slice of FIG. 2B taken at 2B-2B is similar to that of cross section 2A-2A except that the guides 210 are not present because, in this variant, they are not needed along the entire length of the shaft 106.

The cross sectional slice of FIG. 2C taken at 2C-2C is also similar to that of cross section 2A-2A except, because this section is beyond the entry point for the infusion fluid the fluid infusion channel 204 is no longer present. In addition, this portion of the shaft will be situated above the handle 102 so, as will be described later, the return channel 206 is open 212 to the handle 102 for reasons that will become evident below. It also contains a pair of handle guides 214 that allow for attachment/detachment of the handle or shaft relative to the other, and guides 210 (similar to that shown in FIG. 2A) for a proximal portion of the wire loop apparatus.

The cross sectional slice of FIG. 2D taken at 2D-2D is similar to the lower portion of FIG. 2C with respect to the handle guides 214 and also includes a handle cap portion 216 and a trolley guide 218 to receive the trolley 110 mechanism.

FIG. 3 illustrates, in simplified form, the trolley 110 mechanism for the variant of FIG. 1. As shown, the trolley mechanism may be of solid (FIG. 3A) or hollow (FIG. 3B) cross sectional configuration (or some combination thereof) and includes a companion insert port 302 for the port 202 referred to in FIG. 1 through which a telescope or other viewing apparatus can be inserted, an exit port 304 that will guide and align the telescope or viewing apparatus for proper engagement with the channel or port 202 of the shaft 106, a pair of rails 306 on each side that conforms in shape to the trolley guide 218 of the shaft 106, for example, the sliding "v-groove" arrangement shown, a pair of stops/handles 310 that can be used to move the trolley 110 through its range of motion along the longitudinal axis of the shaft 106 and act as a forward-movement limiting element, and a constraining arrangement 312a, 312b that will clamp, affix or otherwise constrain the telescope or viewing apparatus (once fully inserted) in a particular orientation.

As shown, the telescope or viewing apparatus can be anchored to the trolley by a grooved nipple-pin pit 312 at the proximal end. Two grooved pits 312a, 312b are seen on the proximal end, one above, and one below the channel 314 between the two ports 302, 304. These grooved pits 312a, 312b accept the anchoring pin found on conventional scopes, and through provision of two such pits 312a, 312b, allow for rotation of the scope through 180° to allow for viewing in either a downward or upward inclination when, for example, angled scopes of, for example, common angles such as 12°, 30°, or 45° are used. This feature aids in oblique optical targeting through the opening or resection port 124. With and angled scope and the scope attachment pin in the inferior pit 312a, the scope is thus directed to an upward viewing angle providing, with those variants, a direct line-of-sight through resection port 124 to the target area for direct optical targeting.

Advantageously, by affixing the telescope or viewing apparatus to the trolley 110 movement of the trolley 110 along the guides 218 will effect equal movement of the portion of the telescope or viewing apparatus in the shaft 106 towards or away from the distal end 114. In this manner, the trolley 110 provides an external visual indication of the location of the end of the telescope or viewing apparatus.

At this point it should be noted that the telescope or viewing apparatus per se is conventional in the sense that numerous types are already well known and regularly used in performing various types of surgery. The particular type of apparatus, be it a telescope, fiber optic or other device, is conceptually unimportant for an understanding of the invention so long as an appropriate one is selected in terms of size, bevel angle if applicable (i.e. 0°, 12°, 30°, etc.), field of view, type, etc. so as to be compatible with the concepts described herein. Moreover, as will be discussed below, in some cases, two or more different telescopes or viewing apparatus may be used, for example, to change among different conventional bevel angles. Thus, except as is specifically pertinent to an understanding of the invention, particular details regarding the telescope or viewing apparatus are omitted for both brevity and simplicity.

Figure 4:
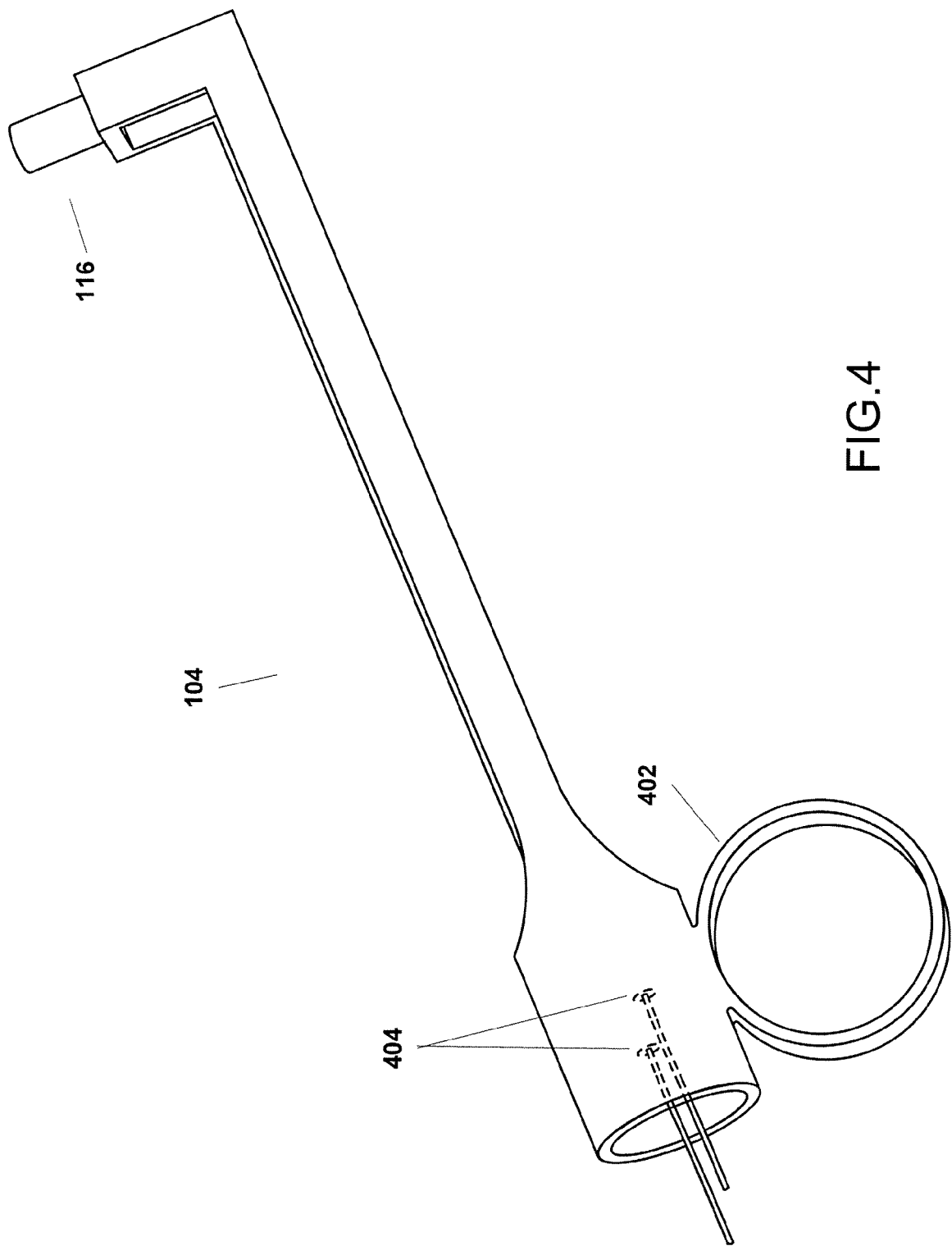
FIG. 4 illustrates, in simplified form, the example control mechanism for the instrument of FIG. 1.

FIG. 4 illustrates, in simplified form, the example control mechanism 104 for the instrument of FIG. 1. As illustrated, the control mechanism 104 includes a movement ring 402 that is used to maneuver a cutting member (described below) through its range of motion via a connection 404 thereto. In addition, the control mechanism 104 can be arranged to cooperate with or constrain the trolley mechanism as necessary to effect the desired operation. In addition, in this particular variant, the control mechanism optionally includes a power connection 116 through which power can be supplied to a cauterization element which may or may not be the cutting member.

Figure 5:
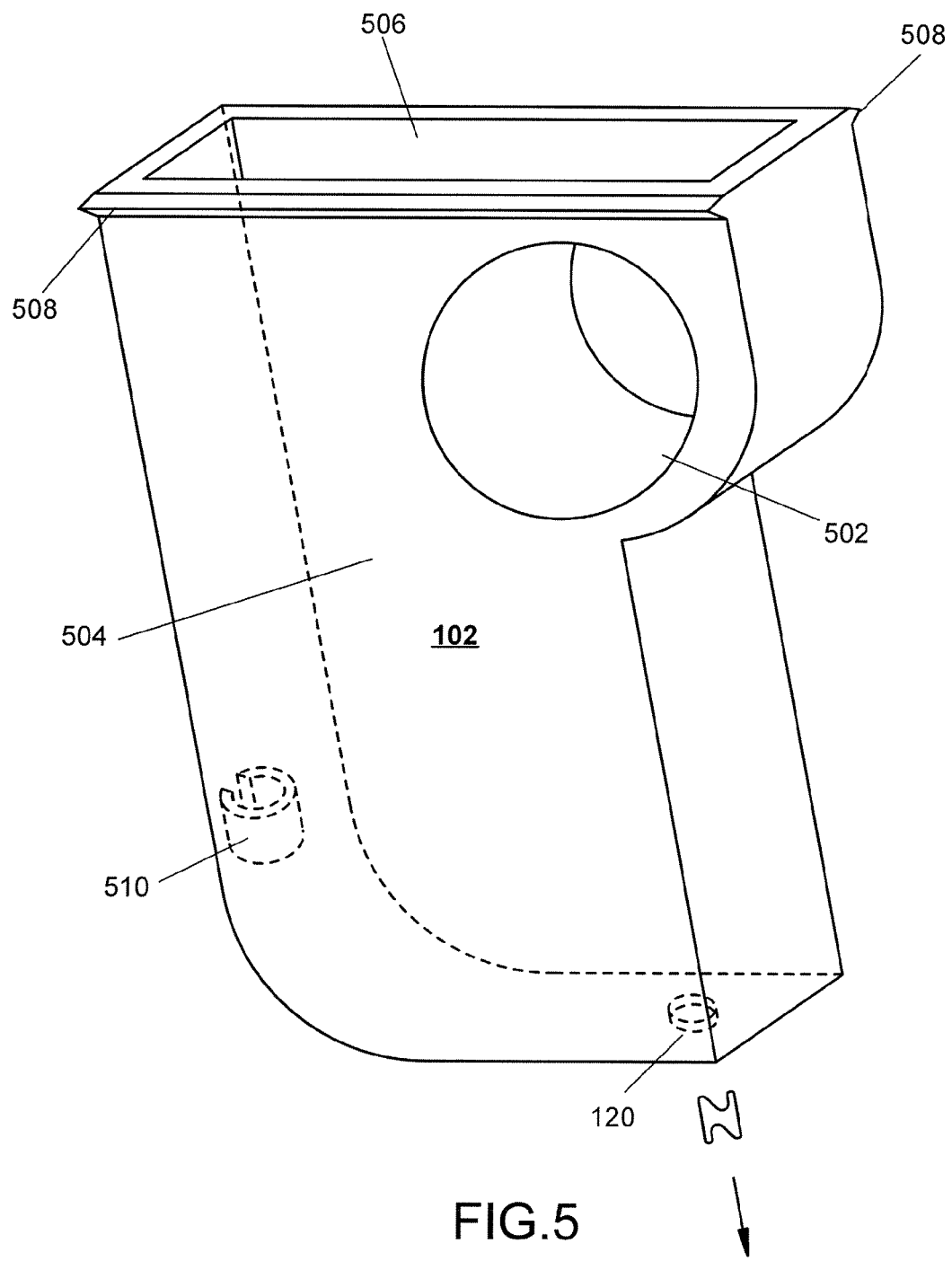
FIG. 5 illustrates, in simplified form, an example handle 102 for the resectoscope variant of FIG. 1.

FIG. 5 illustrates, in simplified form, the handle 102 for the resectoscope variant of FIG. 1. As shown, the handle 102 includes an optional finger hole 502 that facilitates manipulation of the resectoscope 100 during insertion or while in use. In addition, the handle 102 has an internal cavity 504 of sufficient size to enable capture of the resected tissue entering via the return channel 206 through an opening 506 in the top of the handle 102 while allowing for the unobstructed, filtered exit of the return fluid via the vacuum port/fluid outlet 120. In addition, as noted above, the handle 102 also has a pair of rails 508 on each side of the upper portion that conforms in shape to the handle guides 214 shown in the cross sections of FIG. 2C and FIG. 2D.

As shown, the handle 102 for this variant also optionally includes a fluid inlet hose guide 510 that keeps the fluid inlet hose out of the way.

FIG. 6 illustrates, in simplified form, a top view of a portion 600 of the distal end 114 of the shaft 106 near the tip 602. Note that, for clarity of presentation, internal details have been omitted from this view. As can again be seen from this view, the distal end 114 is formed so as to have a physically closed blunt shape 122. In addition, as shown in more detail in FIG. 6, the shaft 106 includes an opening or resection port 124 of a geometrically closed shape that is located on a surface 126 of the shaft 106 near the distal tip 602. In particular, as illustrated in this variant, the opening or resection port 124 is located immediately above, and defines a working area for the underlying cutting member and has a longitudinal length λ that is typically equal to or slightly less than the range of movement of the cutting member, in this case, between its proximal and distal limits.

It should be understood that the size, shape and exact location of the opening or resection port 124 may vary depending upon the particular implementation or intended use. Similarly, a sliding shim or cover plate can be incorporated, for example, to provide size or shape adjustability, and even, in some cases, to close off the opening or resection port entirely, for example, to facilitate insertion into body cavities where the opening or resection port in and of itself could cause trauma during insertion or withdrawal. Depending upon the particular implementation, in some variants, the movement of the shim or cover plate can be tied to that of the telescope so that when the scope is fully extended the shim or cover plate will close off the opening or resection port 124 entirely or at least cover the cutting member itself. Optionally, for some applications, it may be desirable to ensure that a seal is formed between the periphery of the opening or resection port and the tissue about the tissue that would be resected, for example, when used in an application such as removal of tissue from a sinus or the trachea which are both fairly rigid. In such cases, this desire can be accommodated in any of multiple ways. One example approach can involve making some portion of the shaft about the periphery of the opening or resection port slightly flexible so that it can conform to the abutting tissue. Another example approach can involve use of a deformable "gasket" material 606, such as a closed cell foam, putty, gel or other appropriate non-toxic deformable material. Depending upon the particular use, such deformable material can be part of the shaft itself or provided separately, that latter being advantageous for those cases where a surgeon may wish to have the option to do so up until about the time that insertion of the shaft begins.

In addition, and advantageously, some variants may be implemented in a kit that includes only certain components, for example, a shaft by itself, a shaft and handle, a shaft and associated cutting member, different length shafts, or multiple shafts of different lengths, cross sectional shapes and sizes, flexibility, curvature, or that each have openings or resection ports of a different size and/or shape so as to better match or accommodate the size and shape of the tissue to be resected and assist in confining the resected tissue within the shaft so that, it can be conveyed along the shaft 106 for capture in the handle 102.

Still further, in some cases it may be desirable to have a more modularized shaft, in that, the shaft itself would be made up two or more separable pieces, an extension section 608 representing the bulk of the shaft length, and a shaft module 610 containing some or all of the shaft components described herein as being located between the distal end and a location to the proximal side of the working area. In this manner, a particular shaft module 610 could be used, for example, with different length or flexibility shaft extensions 608 or different configuration modules 610 could be used with a common shaft extension 608 in a mix-and-match manner as needed or desired. In addition, this approach provides further advantages in terms of the ability to be produced, production cost and configuration flexibility.

As illustrated by way of example, the opening or resection port 124 is of ovoid shape and the shaft is of a length and cross section appropriate for resection of tissue within the uterus. Advantageously, and irrespective of the dimensions of the shaft 106 or particular shape of the opening or resection port 124, the opening or resection port 124 defines the only zone for interaction between the cutting member and the tissue to be resected while acting as a passive port for removal of fluid from the tissue area or body cavity.

Moreover, depending upon the phase of resectoscope use, the opening or resection port 124 will create the path for regulation of the "inflation", if any, of the cavity where the resection will occur by acting as the outlet (from the perspective of the body cavity) for excess inflation fluid and/or will serve as a passive functional portal for fluid and/or tissue. Optionally, one or more small pore(s) 604 can be provided, that couple to the return channel 206, to provide an additional or alternative route for fluid external to the shaft to pass into the return channel 206, for example, during an inflation phase where it may be difficult or undesirable to do so through the opening or resection port. Depending upon the particular implementation, such pores can be sized small enough so that they do not de-inflate the cavity during working or, alternatively, can be selectably blocked for example, by the slidable shim or some other means, so as to only be open at a particular time, for example, only when, as will be described below, the telescope or viewing apparatus is in the extreme distal position or when a switch is in a position where infusion fluid is routed out of the shaft for purposes of inflation or irrigation.

FIG. 7 illustrates, in simplified form, an external end view of a blunt distal end 122 portion 700 of the shaft 106. As can be seen from this view, at least a portion 702 of the tip 602 is optically transparent so as to act like a window and is aligned with the channel or portal 202 for the telescope or viewing apparatus so as to provide for forward viewing through the distal end portion 702 via the telescope or viewing apparatus under the appropriate conditions.

Depending upon the particular implementation, the optically transparent portion 702 can simply be a hole or it can be a physical element. In the case of a physical element, it can be an integral part of the shaft, for example, if at least that portion of the shaft is, or is made, transparent, or it can be a separately formed and inserted element, like a membrane, a piece of plastic or glass (whether flat or lens shaped) or other optically transparent material. Moreover, in some cases, this portion 702 or window area can be, in whole or part, a lens that can work in conjunction with the telescope or viewing apparatus to provide a different field of view than would be provided by the telescope or viewing apparatus alone. For example, the window area 702 could be an element that is flat or convex on the external side of the distal end 122, but flat and beveled at a specified angle on the internal side (i.e. inside the shaft) so that a comparably opposite beveled end of the telescope or viewing apparatus can be butted against it to allow for straight-ahead, angled or wide-field viewing (as determined by the shape of the external side) when the trolley 110 is in the extreme forward position.

Alternatively, by appropriate sizing, the window area 702 can be a hole that, for purposes of insertion, can be filled or blocked by the end of the telescope or viewing apparatus itself through maintaining it in a suitably spaced extreme forward position.

Optionally, the auxiliary channel 208 can be carried forward to the distal end 122, such as is shown. Additionally or alternatively, as shown in this variant, the portion 702 is ringed with an electrical conductor 704 that can be selectively connected to a power source to directly effect cauterization while viewing the tissue to be cauterized through the distal end 122.

Figure 8:
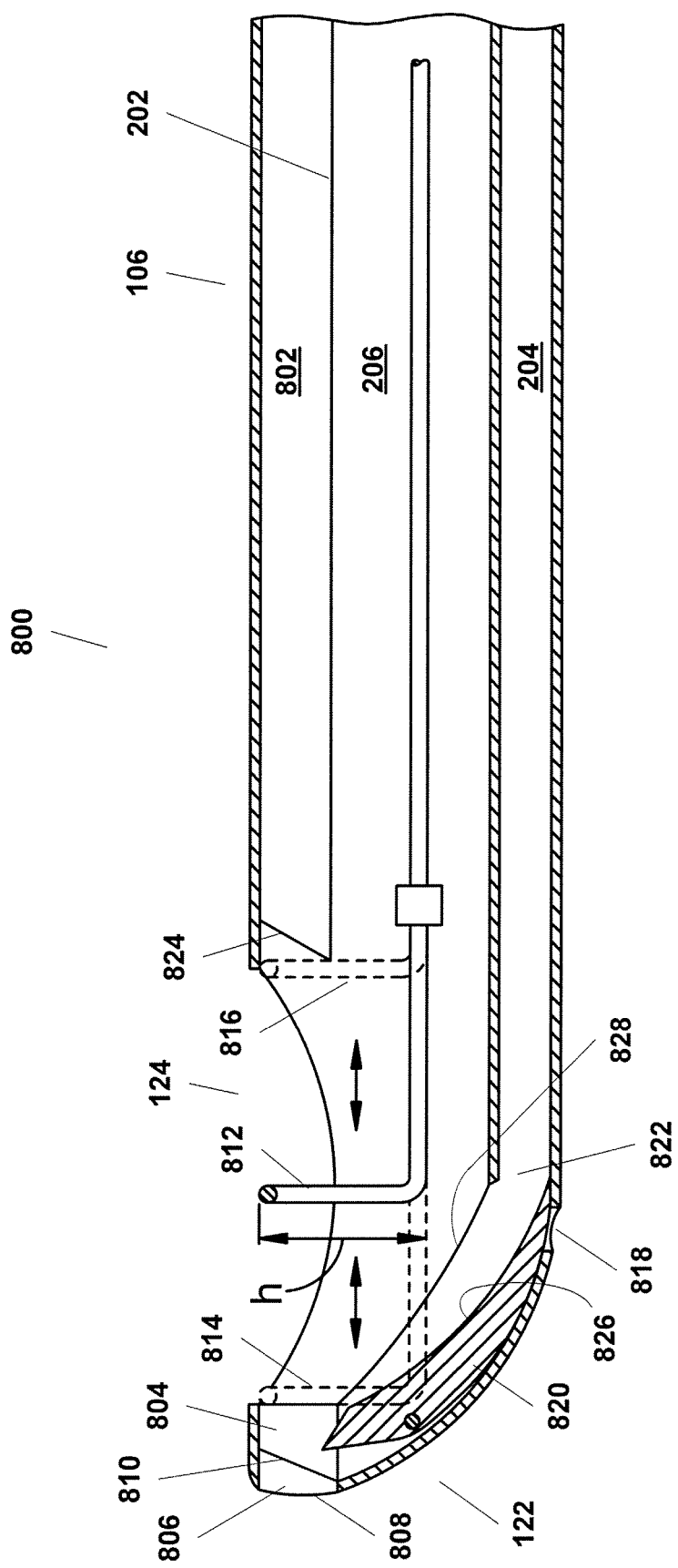
FIG. 8 illustrates, in simplified form, a longitudinal cross section of the portion of the shaft of FIG. 6.

FIG. 8 illustrates, in simplified form, a longitudinal cross section of the portion 800 of a shaft 106 of one example variant. In FIG. 8, the longitudinal fluid infusion channel 204 and return channel 206 can be readily seen as can the blunt nature of the distal end 122. Although a single fluid infusion channel 204 is illustrated for simplicity, in some variants, two or more separate inflow channels with combined or associated individual respective controls could alternatively be used. In addition, a telescope 802 having a 30° bevel resides in the telescope channel 202, at a retracted location, and is aligned with the telescope end portal 804. In this variant, the telescope end portal 804 is capped with a lens 806 that is slightly convex on its outer surface 808 and beveled 810 at a mirror image 30° bevel so that, at the extreme extended position, the end of the beveled telescope 802 and the internal surface if the lens 806 will mate.

The opening or resection port 124 described in connection with FIG. 5 is also clearly visible.

A cutting member 812 also resides within the shaft 106. Depending upon the particular intended use and implementation, the cutting member 812 can be a wire loop (such as shown), a sharpened blade, a rotary cutting implement, a micro-vibrational or harmonic or shutter-type cutting device, or other cutting implement (each with or without cauterization capability). Alternatively or additionally, the particular cutting member 812 can be configured for movement in an arcuate, axial, rotational, diagonal, transverse, reciprocating or other manner to effect cutting in a direction other than through pure longitudinal movement.

In yet other variants, the cutting member 812 can be configured so that its orientation within the shaft 106 is changeable to provide for cutting at two or more different angles. In such variants, an auxiliary or reconfigurable telescope or viewing apparatus may be necessary or desirable to allow for angulation.

Depending upon the particular implementation, the cutting member can be supplied with, and integral to, the instrument or shaft as packaged or it can be of a separately provided snap-in and/or snap-out design.

Irrespective of the particular cutting member 812 used, its mode of integration with the shaft, and its direction of movement or orientation, the cutting portion of the cutting member 812 is wholly constrained within the shaft. Moreover, ideally the cutting member conforms, through at least a part of its range of motion, to either an inner or outer surface 126 of the shaft 106 and/or an imaginary surface of the opening or resection port that would be formed if the shaft contour was continuous across the region of the opening or resection port. Thus, if the shaft near the opening or resection port is arched, because the shaft is circular or oval in cross section, the cutting member will typically have a similar or lesser arch. If the shaft near the opening or resection port is flat or near flat, the cutting member can be similarly contoured in shape.

However, if a type of cutting member 812 other than a wire or blade is used, for example a micro-vibrational or harmonic cutter (i.e. a harmonically vibrated blade), scissor or shutter-type mechanism, the cutting member may not follow the contour. This is not a problem, as following the contour is not critical to implementation of the invention but highly desirable for some implementations or intended uses. Rather, the important aspect is that the cutting member 812 remains within the working area, whether or not the cutting member 812 is a blade, loop, scissor, shutter, harmonic or other type of cutting mechanism.

For purposes of illustration, as shown in the variant of FIG. 8, the cutting member 812 is a wire loop that is moved by longitudinal movement of the forefinger loop 402 on the control mechanism 104 near the handle 102 and is constrained against non-longitudinal movement by the guides 210 of FIG. 2. As should be understood from FIG. 8, the cutting member has a height "h" that keeps it wholly within the shaft 106 through its range of motion from a fully distal position 814 to a fully proximal position 816 and, in this variant, is curved in an arc of approximately a 4 mm radius so that the telescope or viewing apparatus 802 can pass through and underneath the cutting loop with minimal to no contact therewith. In this regard, it should be noted that, at either or both extremes 814, 816, the cutting member 812 may or may not be visible through the opening or resection port 124. As a result, the cutting member 812 can "guarded" by the outer surface 126 of the shaft 106, thereby preventing it from causing undesirable laceration or puncture of tissue during insertion or at any point in the procedure where cutting is not warranted or desired. Still further, through this configuration, the outer surface 126 of the shaft 106 limits the depth of cut, again greatly reducing the risk of undesirable laceration or perforation.

In addition, in this variant, the shaft 106 includes one or more fluid export pores 818 and a fluid routing switch 820 with the fluid export pore(s) 818 being under the fluid routing switch 820 and beyond the termination point 822 of the fluid infusion channel 204. The fluid export pore(s) 818 can be of any geometric shape(s) or number.

As shown in FIG. 8, the fluid routing switch 820 is a binary position pivoting switch that is sized and shaped so that, in one position (the infusion position), the switch will direct a substantial portion, if not all, of the fluid passing through the fluid infusion channel 204, from the proximal end towards the distal end, and out through the fluid export pore(s) 818, for example, in the case of a device for intrauterine resection, to inflate the uterus. In the other position (the circulation position), the switch 820 will substantially, if not completely, inhibit fluid flow out of the pore(s) 818 and instead, direct fluid into the return channel 206 in the vicinity of the opening or resection port 124. As illustrated in this variant, the switch 820 is normally biased into the circulation position. Advantageously, this allows the end 824 of the telescope or viewing member 802 to be used to actuate the switch 820 and divert the infusion fluid out the pore(s) 818.

Optionally, in some variants, the internal surface 826 of the switch 820, about the switch 820, and/or surfaces 828 facing the return channel 206 (whether or not there is a switch) can be specifically inclined and polished or otherwise made reflective so as to act like a mirror and enable a further or additional range of view through the opening or resection port than could potentially be available using only the telescope or viewing apparatus (i.e. provide accessory optical capability for, for example, tissue targeting or cauterization).

Alternatively, in other variants, the fluid routing switch within the shaft 106 can be dispensed with entirely.

Figure 9:
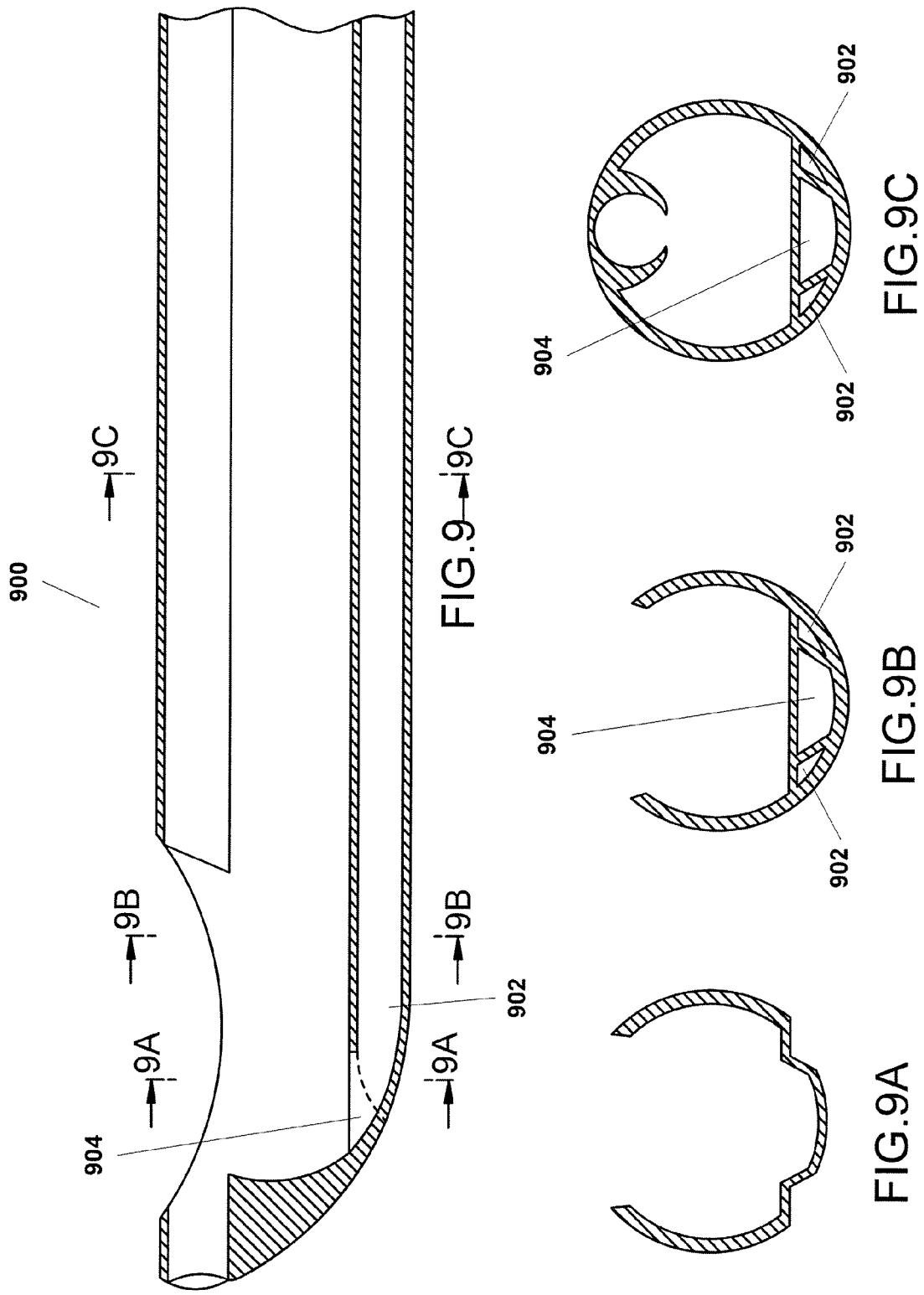
FIG. 9 illustrates, in simplified form, an alternative "switchless" variant.

FIG. 9 illustrates, in simplified form, a "switchless" (with respect to the shaft) variant 900 by employing at least two separate fluid inflow channels 902, 904 routed to effectively create the two flow patterns obtained by the switch. In other words, at least one of the fluid inflow channels 902 is connected to the export pore(s) (analogous to one of the binary switch positions) and another of the fluid inflow channels 904 is configured to cause fluid to remain within the shaft and flow into and through the working area (analogous to the other binary switch positions). Such a switchless variant has the advantage that, with respect to the shaft itself, fluid routing becomes a passive function, formation of the shaft becomes simpler and a moving part is eliminated. As a result, it is easier to create an inclined polished or mirror area within the shaft as described above.

Of course, such a "switchless" approach would still require some form of selection element which could be located, for example, on or adjacent to the handle, the control mechanism, or wholly external to the resectoscope itself. In addition, this alternative approach enables specific control of the flows so that a dual or combination flow can optionally be achieved (i.e. an intermediate point between full output through the infusion port and full circulation flow at a desired flow rate).

Figure 10:
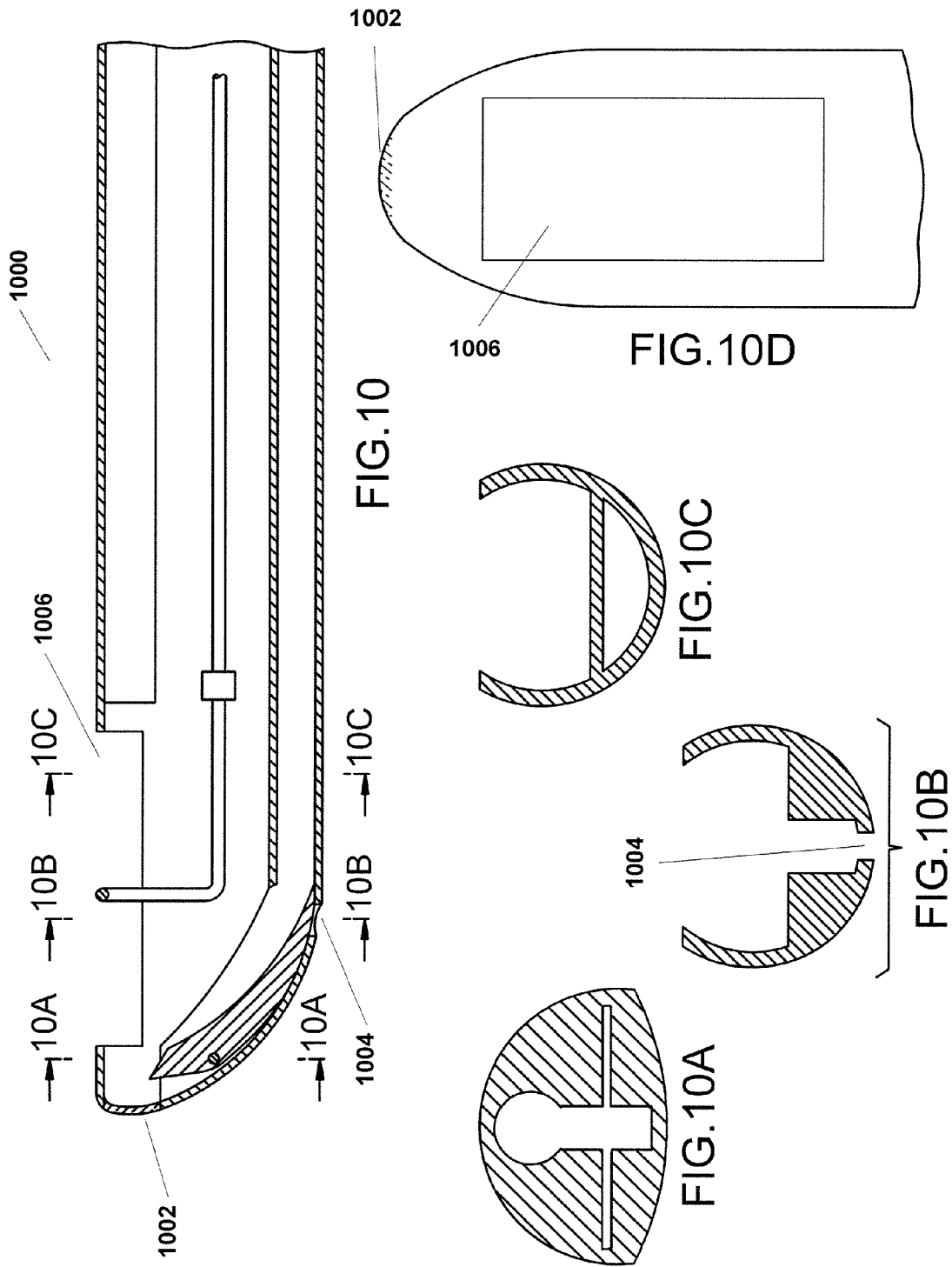
FIG. 10 illustrates, in simplified form, another alternative variant.
Figure 17:
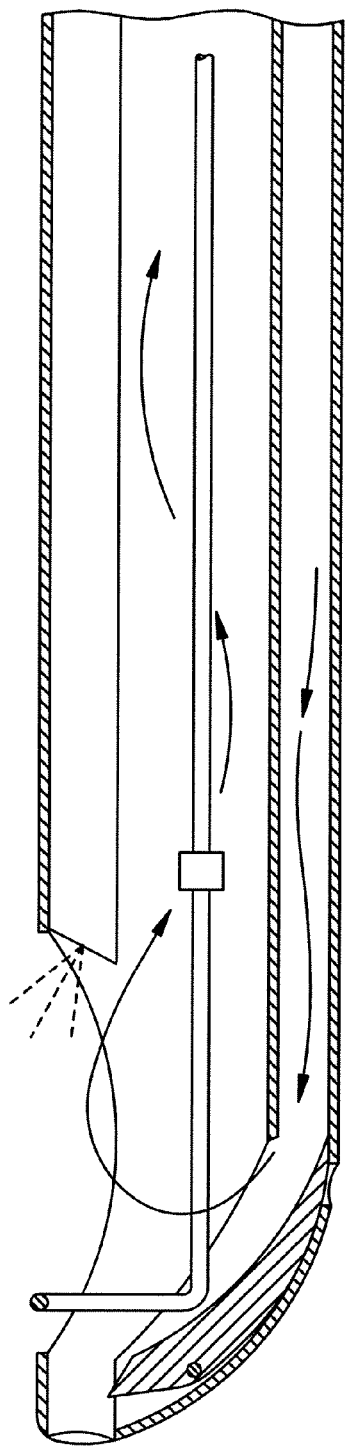
Figure 18:
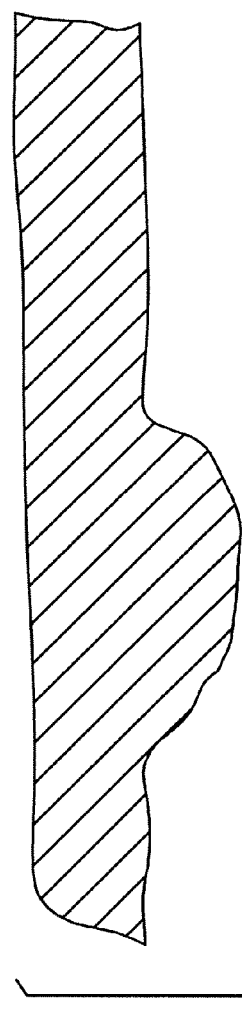

FIG. 10 illustrates, in simplified form, an alternative shaft portion 1000 variant that is similar to that of FIG. 8 except a portion of the distal end 1002 is itself transparent, so no separate membrane, lens or other cap is required, there is specifically one circular infusion pore 1004, and the opening or resection port 1006 is rectangular. For completeness, FIG. 10A is a cross sectional slice of the shaft taken at 10A-10A (through the pivot point of the switch), FIG. 10B is a cross sectional slice of the shaft taken at 10B-10B (through the infusion pore), and FIG. 10C is a cross sectional slice of the shaft taken at 10C-10C (through a portion of the opening near the proximal working area limit for the cutting member). In addition FIG. 10D illustrates a view of the upper surface of the shaft 1000 taken from above the opening or resection port 1006.

FIG. 11 illustrates, in simplified form, a longitudinal, cross sectional side-view of a further alternative shaft portion 1100 variant that uses a sliding reed as the fluid routing switch. In addition, in this particular variant the reed also optionally defines and segregates the fluid infusion channel 1102 from the return channel 1104. For ease of understanding this variant, example cross sectional slices, taken at 11A-11A through 11G-11G, are also provided in FIG. 11A through 11G. For further simplicity, details such as the cutting member, its constraint and movement control, as well as any optional additional auxiliary channel(s) have been omitted but it should be understood that any or all of them could also be present.

In this variant, two fluid export pores 1106, 1108 are provided and are best illustrated in FIG. 11E. As illustrated in the various cross sectional slices, the fluid infusion channel 1102 splits into a pair of smaller channels 1110, 1112 as it approaches the distal end 1114 in order to reach the two fluid export pores 1106, 1108. Fluid infusion into the body cavity occurs via fluid flow from the fluid infusion channel 1102, through the two channels 1110, 1112 to the fluid export pores 1106, 1108. Again, it should be understood that each individual fluid export pore 1106, 1108 could be readily implemented as two or more individual pores. Alternatively, fluid circulation occurs via a fluid circulation channel 1116 that is located between the two smaller infusion channels 1110, 1112 and is shaped to direct the fluid into the vicinity of the working area 1120 for return down the return channel 1104.

Of course, it should be understood that, in other implementation variants, the fluid circulation channel could be split up into the two channels and the fluid infusion channels could be the central channel, the only differences being a potential change in relative sizing of the channels, the export pore(s) would be centrally located and there would be two portions used to direct the flow into the working area to account for the split channels.

The above two variants reflect a desire for longitudinal symmetry about the vertical. However, it should be understood that symmetry is not required and, in some variants, asymmetry may provide advantages for particular uses or applications, for example, to cause a turbulent or specific pattern of flow near the distal tip or working area. In such cases, some form of side-by-side arrangement or other arrangement would likely be used.

As noted above, one example variant mechanism for switching of fluid flow is comprised of a blade-like control reed which spans the hollowed shaft 106 transversely. The control reed also spans from proximal to distal within the shaft along the greater length of the instrument, and is held in place by small lateral grooves 1118 along the inner wall of the shaft. The control reed is capable of sliding longitudinally distally and proximally along the shaft. FIG. 12 illustrates, in simplified form, an example sliding control reed 1200 configured for use in conjunction with the shaft portion of FIG. 11. As illustrated, when the control reed 1200 is within the shaft 106, it will create an eccentric partition axially along said shaft such that the inflow channel 1102 lies beneath, and the larger outflow/return channel 1104 lies above the control reed 1200 along the length of the shaft 106. Depending upon the particular implementation, the control reed 1200 may be flat, such as shown, or may be curved in some manner to, for example, increase the diameter of the overlying return channel 1104, or contribute to the overall stiffness of the instrument 100. Similarly, depending upon the particular design, control reed material or intended use for the instrument, the control reed 1200 itself can be reinforced, for example, by fins, ribs, or a differing thickness across its width or along its length to increase stiffness or create a specific flexure pattern.

The control reed 1200 accomplishes its switching task through use of holes 1202, 1204, 1206 located near its distal end 1208. The holes 1202, 1204, 1206 are placed, sized and shaped to effect the desired fluid flow control based upon the position of the control reed 1200 at a particular point in time. As illustrated, a center hole 1202 is located near the distal end 1208 of the control reed 1200 and provides a flow path up and into the working area 1120 when the center hole 1202 is aligned, in whole or part, with the fluid circulation channel 1116. In addition, the center hole 1202 is located relative to the end of the reed 1200 so that the control reed 1200 can be placed in a position where an element 1122 blocks all flow through that hole 1202. As illustrated, that position is an extreme forward (i.e. distal) position, but could alternatively be a rearward position or some position in between.

In addition, the control reed 1200 contains a pair of lateral holes 1204, 1206 to either side that can be aligned with the infusion channels 1110, 1112 to direct fluid flow from the main fluid infusion channel 1102 to the export pore(s) 1106, 1108. As with the center hole 1202, the lateral holes 1204, 1206 are located on the control reed 1200 so that they can, based upon the position of the control reed 1200, provide a fluid flow path, in this case between the infusion channel 1102 and export pore(s) 1106, 1108 (in this variant, in the vicinity of the shaft 106 at the cross section taken at C-C), or to cut off all flow to the export pore(s) 1106, 1108. As illustrated, in cross section B-B, in this variant, solid protrusions 1124, 1126 above the control reed groove 1118 are positioned act so as to block flow through the lateral holes 1204, 1206 when the control reed 1200 is at its most proximal operational setting. Of course, as with the central hole 1202, this lateral hole 1204, 1206 blockage could also occur at a forward position or some position in between.

For purposes of understanding, in the variant of FIG. 11 and FIG. 12, the distal end 1208 of the control reed 1200 and distal end slot 1128 are arranged so that the control reed 1200 can move a distance essentially equal to, or slightly more than, the diameter of the central hole 1202. With the control reed 1200 in its proximal position, the lateral holes 1204, 1206 are blocked and the central hole 1202 is open to accomplish an internalized fluid circuit. Thus, with the control reed 1200 in the proximal position, fluid will be passively directed from the inflow channel 1102 into the center channel 1116, creating a flow circuit within the instrument's shaft 106. In the variant illustrated in FIG. 11, when assembled and in use, fluid flows in the distal direction from the inflow channel 1202 under the control reed 1200, and then upward via a curved surface 1130 within the center channel 1116 proceeding out through the center hole 1202 in the overlying control reed 1200. The fluid then flows or is drawn proximally into the outflow/return channel 1104 with or without vacuum assist. This is the typical control reed 1200 position for resection.

In its distal position, the lateral holes 1204, 1206 of the control reed 1200 are open while the central hole 1202 is blocked by the distal end slot 1128 so that fluid will be routed out the export pore(s) 1106, 1108. Thus, as the control reed 1200 is moved to block the center hole 1202, the nearest 1206 of two lateral pores 1204, 1206, one on each side, will move from under the blocking surface 1124, 1126 and thus allow diversion of flow up and into the lateral channels 1110, 1112 whose ultimate path leads to the export pore(s) 1106, 1108.

Depending upon the particular implementation, movement of the control reed 1200 can be integral with movement of the telescope or viewing apparatus 802 or not. As shown, the sliding control reed 1200, when within the shaft 106, is activated from the proximal end of the instrument by an open linkage mechanism (not shown) to the trolley 110, and is automatically activated with full advancement of the scope/trolley in unison. The control reed 1200 is pushed forward by the trolley 1110, or independently by a finger leaving the trolley 110 in its home/resection position. This allows, for example, uninterrupted re-inflation of the tissue cavity while keeping the telescope or viewing apparatus 802 in a diagnostic or targeting mode or during active resection, as desired. Alternatively, movement of the control reed 1200 can be made independent of the other components, for example, the telescope or viewing apparatus 802. This can be accomplished in a straightforward manner by providing an element at or near the proximal end of the shaft 106 that is connected to the control reed 1200 and thus, its movement will move the control reed 1200.

Advantageously, some variants using the control reed 1200 arrangement for fluid switching will thus, have the ability to provide variable flow, not readily obtainable via internal switching alone with the preceding mechanical switch by: a) design, through placement, sizing and shape of the holes themselves so that, for example, there is an inverse linear ratio of diversion between completely internalized and externalized flow as the control reed is moved, b) movement of the control reed into any of an infinite number of intermediate positions irrespective of the particular flow relationship provided by the hole placement, shape and sizing, or c) both. As a result, finely controlled flow splitting between internalized and externalized routes can be achieved, for example, in order to maintain slow balanced cavity infusion while concurrently performing resection with vacuum assisted evacuation and/or tissue export.

In general, the approach to controlling the fluid flow that is used to convey the resected tissue from the working area towards the handle 102 will likely vary depending upon the particular implementation and intended use. For example, in some cases, the control can be fully manual. In other cases it can be a result of movement of another element, for example the telescope or viewing apparatus of FIG. 8 or the movement of the cutting member itself. In yet other cases, the control can result from a combination of manual adjustment based upon mechanical, electric or electronic feedback. In yet other cases, fully automated control is possible through use of, for example, electrically activated fluid gates, electromagnetic, mechanical, hydraulic, or other switches. In some variants that use a distally placed switch that is not directly manipulable via an external control, the switch can be designed to be externally controlled through fluid flow itself in conjunction with vacuum, or through only positive pressure fluid flow (i.e. without the use of vacuum at all). In addition, and advantageously, when in the fluid circulation mode or configuration (i.e. fluid will not flow generally out the export pore(s)) flow rates of 100 cc/min or more can be used and, with vacuum boost, instantaneous flow rates within the shaft can exceed 4000 cc/min.

FIG. 13 illustrates, in simplified form, a cutaway view of a shaft portion 1300 for a resectoscope, that is similar to the shaft portion 800 of the resectoscope of FIG. 8 except that the distal end has a window area 702 that is made up of a transparent membrane 1302 instead of a lens 806. As illustrated the shaft portion 1300 is configured as it would look during insertion. In this configuration, the telescope or viewing apparatus 802 is fully extended (i.e. the trolley 110 has been moved to its forward limit position so that viewing out the window area 702 of the shaft 106 is possible using the telescope or viewing apparatus 802. The cutting member 812 is in its "home" position which, although illustrated as being at the distal limit 1306 (due to the surgical convention of preferably only cutting in the distal to proximal direction due to the puncture risk inherent with conventional devices) it could alternatively be at a proximal limit or somewhere in between. In the fully extended position, the telescope or viewing apparatus 802 impinges against the upper portion 1304 of the switch 820 thereby opening the fluid export pore(s) 818 to the fluid input channel 204 to allow fluid to pass out of the shaft 106 while preventing infusion fluid from directly entering the return channel 206 from inside the shaft 106.

Advantageously, it should be recognized that variants configured in this manner can be used in circumstances where organ "inflation" may or may not be necessary. For uses where inflation is not necessary, this is accomplished by limiting trolley 110 movement or clamping the telescope or viewing apparatus 802 such that, when the trolley 110 is in the fully extended position, the telescope or viewing apparatus 802 will fall just short of the upper portion 1304 and thus avoid actuating the switch 820. Although, by doing so, this could result in some minor reduction or distortion in the forward field of view due to the gap between the end of the telescope or viewing apparatus 802 and the window area 702, any such reduction or distortion will likely occur, if at all, at the periphery of the field of view so the reduction will have minimal to no impact in most cases.

FIG. 14 illustrates, in simplified form, the portion of the resectoscope of FIG. 13 as it would look during the "working" or resection process. As shown, in this configuration, the telescope or viewing apparatus 802 is at or near its fully retracted position and, as a result, the switch 820 will block passage of fluid to the fluid export pore(s) 818 and cause the infusion fluid to circulate up into the return channel 206 where the applied vacuum will cause it to traverse towards the proximal end of the shaft 106. Moreover, the placement of the telescope or viewing apparatus 802 allows for unobstructed view of the opening or resection port 124 as the cutting member 812 is moved throughout its range to perform unidirectional or bi-directional resection. In addition, since they are independently maneuverable, the end of the telescope or viewing apparatus 802 can be used to "clear" or dislodge any resected tissue pieces that may get caught on the cutting member 812 by simply moving the two with respect to each other so that the telescope or viewing apparatus 802 passes by the cutting member 812. Still further, should the end of the telescope or viewing apparatus 802 become partially or totally obstructed by tissue or clouded by turbid fluid from the resection (if any), the telescope or viewing apparatus 802 can be moved forward of the cutting member 812 and into the clean flow of infusion fluid, thereby cleaning the end without the need to withdraw the shaft 106 of the resectoscope 100 or the telescope or viewing apparatus 802 from the body cavity.

Alternatively or additionally, in instances where there are one or more optional auxiliary channels 208 present and a piece of tissue or debris becomes stuck on the cutting member 812 or telescope/viewing apparatus 802, a stylet can be passed through an auxiliary channel 208, in order to bump the cutting member 812 or piece of stuck tissue or debris and dislodge it from the cutting member 812 or telescope/viewing apparatus 802. Alternatively, a home position "groove" or recessed area, configured to closely conform to and accept the cutting member 812, can be used to aid clearing of stuck tissue or debris from the cutting member 812 through return to this home position.

FIG. 15 illustrates, in simplified form, the portion 1300 of the resectoscope of FIG. 13 wherein the telescope or viewing apparatus 802 has been moved ahead of the cutting member 812 as described above.

FIG. 16 illustrates, in simplified form, the portion 1300 of the resectoscope of FIG. 13 in an optional third configuration. In this configuration, the resectoscope is optionally designed to lock the cutting member 812 at a position within the working area—illustratively shown in this example for simplicity at the midpoint of the range of motion. In this position, the cutting member 812 can be connected to a power source to effect cauterization or, for example in the case of a cutting loop as shown in FIGS. 8 and 16, drag cutting of tissue (i.e. along a plane formed by the cutting member 812 or angled from that plane within an angle θ as necessary. Again, it is worth noting that the shaft 106 and/or periphery 1604 of the opening or resection port 124 will act to limit the depth of cut and reduce the risk of unwanted extraneous lacerations.

Of course, in some variants, the cutting member 812 can optionally be configured to cauterize throughout all, or in other variants a limited portion, of the range of movement.

With respect to the use of the resectoscope, operationally, there are generally two home positions for the hand to accomplish the basic movements used to employ many variants of a resectoscope 100 such as described herein.

The first hand-home position is used to advance/retract the telescope or viewing apparatus 802 to/from the diagnostic position. In the diagnostic position, an unobstructed panoramic view beyond the blunt distal tip 122 is provided. To do so, the index and middle fingers grasp the shaft 106 via the grip/stop 108 and the thumb rests on the handle 112 portion of the trolley 110. Movement of the thumb distally is used to advance the telescope or viewing apparatus 802 and movement in the opposite direction is used to retract the telescope or viewing apparatus 802 and, in some variants, that same movement thereby also controls the switch in the distal end of the shaft. In the retracted position, a view of the working area as well as a view external to the shaft 106 via the opening or resection port 124 is provided.

The second hand-home position is used to configure the resectoscope 100 for surgical working (i.e. resection, drag cutting and/or cauterization as well as targeting). In this position, the thumb is typically placed in the handle ring 502 and the forefinger is placed in the ring 402 of the control element 104. Since the cutting member 812 is connected to the control element 104, the cutting member 812 is actuated by movement of the control element 104 via its ring 402 while the instrument is stabilized by the thumb being in the thumb hole 502. Alternatively, in some variants, the working position can involve placement of the index finger in the handle ring 502 (with the remaining fingers wrapped around the back of the handle) and the thumb in the ring 402 of the control element 104. When used in this manner, movement of the thumb will move the cutting member.

Alternatively, the resectoscope 100 is further configured so that the index and middle fingers can pinch the finger grip 108 while the thumb works the control element 104 or the trolley 110 from a side position.

Having described aspects of representative example devices incorporating aspects of the invention, the operation of one example variant will now be described with reference to FIGS. 17, 18, 19 and 20 to illustrate the operation of a resectoscope 100 using such variant with FIGS. 17-20 specifically illustrating, in simplified form, different stages of tissue resection. For simplicity and purposes of contrast with conventional approaches, the operation of one such device will now be described for the same procedure as described above in the "Background" section. As illustrated, the variant of this example employs a hybrid of adjustable positive pressure infusion into the infusion channel from a free flow reservoir, and fluid return through the return channel is vacuum driven with optional boosting.

Just as in any prior method, the patient is positioned with adequate analgesia, the cervix sterilized and dilated, except that here the dilation proceeds directly to the diameter of resection instrument, in this example, around 10 millimeters.

Presuming that a fully disposable version or partially disposable kit version is used, the pre-assembled instrument or the pertinent kit component(s) is/are removed from one or more sterile packages, and if in kit form assembled, and if not simply removed ready for hookup to the telescope 802, power source, and fluid/vacuum lines. After a quick vacuum driven flush, the telescope 802 is positioned to provide a view out the distal tip through the window area (FIG. 13) and the instrument is inserted into the cervix and directly into the uterine cavity with the aid of its blunt, enclosed distal tip without significant concern of laceration or puncture. Advantageously, due to its configuration, should the surgeon encounter cervical polyps during insertion, they can be removed as part of the entry process. Upon insertion to the uterine cavity the usual visual assessments are made with fluid infusion hydrometra.

After the surgeon has done the usual photo documentation and optically identified the areas intended for resection, the instrument is reconfigured into the resection mode by a single hand motion to withdraw the telescope 802 back to the resection position (FIG. 17) and bring the cutting member 812 into position. This also causes the infusion fluid to begin circulating from the infusion channel 204 into the return channel 206. Through minor external adjustment of the infusion fluid flow and return vacuum rates, fluid flow patterns are actively internalized within the shaft 106 and re-made to serve the purposes of resection with concurrent tissue exportation.

Next, the tissue to be resected is brought into proximity of the resection port (FIG. 18), and with optical guidance and low pressure vacuum, contact to the intended area is made.

Now, the protected cutting member is brought into motion (FIG. 19), in this case removing a slice 1902 of tissue. Depending upon the particular patient needs and size of the tissue to be resected, the cutting member 812 may moved through the zone defined by the resection port multiple times taking multiple slices, advantageously, without need for re-positioning or reassessment due to inherent depth control provided by the surface 126 of the shaft 106. The resected tissue slice 1902 passes down the shaft 106 proximally toward the handle assembly via the return channel 206 and, in this implementation, into the handle 102 body through an opening in the channel floor just past the beginning of the fluid infusion port 204, for capture and retention either in the handle 102 itself or an auxiliary container inserted in or associated with the handle 102. In the event a slice of tissue 1902 becomes lodged on the cutting member 812, the telescope 802 can be independently moved forward to dislodge it. Similarly, if smaller fragments or turbid fluid cloud the end of the telescope 802, it can readily be moved into the clean fluid flow for clearing without withdrawal from the patient or concern that pathological tissue will be lost. In addition, a foot pedal actuated vacuum booster can be used in a pulsed fashion to further augment clearance and export of tissue. If necessary, with some implementations, the cutting member 812 can be further cleaned by return to a rest position, for example, if the rest position is at a location of maximum fluid flow or if a mechanical element is provided that is designed to clear the cutting member 812 through relative movement.

After tissue resection to the flush level, the instrument 100 can again be reconfigured to the diagnostic conformation with a single hand motion and without withdrawal of the device from the patient, re-attaining the initial diagnostic conformation, panoramic view, and fluid flow patterns to support post resection reassessment or documentation. Advantageously, with some implementations, if a bleeding vessel is encountered during the process, it can be treated by cauterization using, for example, the cutting member 812 itself with optical targeting, or in other variant implementations where the cutting member 812 can not be used for cauterization, by an electrode that is passed through the auxiliary channel 208 without, as would be required with conventional instruments, disassembly/reassembly to, for example, substitute a roller-ball electrode.

Since, in this example, the resected tissue piece 1902 has been conveyed to and collected in the handle 102, the handle 102 can simply be removed, closed or packaged and the tissue sent for pathological examination without removal from the handle 102. Alternatively, if the handle 102 holds or is connected to some other removable tissue connection receptacle, that receptacle can be removed from the handle 102 or its connection or, in some other variants, the tissue 1802 can be removed from the handle 102 or other collection container and placed in the appropriate receptacle for transfer to pathology for analysis.

Note that, throughout the procedure, no components need be fully withdrawn from the patient and the external shape of the portion of the device contained within the patient does not change.

If all or part of the instrument is disposable, the disposable elements are now discarded. If the device is not disposable, it is disassembled, cleaned, sterilized and repackaged in the conventional manner.

Based upon the above, it should be understood that different variants can be used in many different medical disciplines for different surgical applications. For purposes of understanding, the following identifies some representative examples of some surgical applications that can benefit through use of one or more variants, it being understood that those enumerated are not intended to be exhaustive with respect to the particular discipline or to the specific application(s) within any particular medical discipline.

In the area of cystoscopic and urologic surgery the applications are evident from the foregoing description with the shaft being appropriately sized (length and cross section) for entry into the particular body cavity.

In the area of neurosurgery the invention may be used to enter ventricles, spaces, crevices or between cranial tissue lobes with visual assistance through the blunt enclosed distal tip and, with the telescope or viewing apparatus withdrawn to the working position, to provide for substantially concurrent tissue excision and export from within the particular area. In practice, intracranial spaces would be entered and viewed directly, for example, following a burr-hole craniotomy. Depending upon the particular circumstances a sealing grommet can be placed to allow articulation of the instrument shaft around a soft fulcrum like pivot. For such an application, the shaft would likely be curved or have at least some flex capability to allow it to be maneuvered into spaces as needed.

In order to avoid increased intracranial pressures, where necessary, a brief fluid infusion via the export port(s) can be accomplished concurrent with or prior to incremental advancement of the instrument by using rest phases and fluid pressure decompression to allow for venous cerebral circulation to resume. Utilizing the inherent depth of resection control aspect provided by the resection port, the instrument can biopsy or remove tissues without the need for concurrent cavity inflation once the targeting and positioning movements are finished. Brief fluid re-infusion can then allow for overall assessment of the progress if necessary.

In a similar fashion, variants can be used in microdiscectomy of the spine. Here an appropriately shaped and dimensioned shaft would be passed through a small paraspinal incision through a ligamentum flavum while viewing through the blunt, enclosed distal tip. The shaft end would be inserted between the disc and the nerve accompanied by slight fluid infusion would then provide additional space for movement. The distal section of the shaft would then be positioned so that the solid surface would be positioned away from the disc and used as a retractor. Through peripheral viewing through the working area upon withdrawal of the telescope or viewing apparatus to the proximal side of the working area specific resectable tissue targeting will occur, followed by switching to the fluid circulation mode and shaving or chipping away of disc or spinal tissue with an appropriate cutting member and concurrent tissue export towards the proximal end of the shaft.

In the area of chest and pulmonologic surgery variants could be used in bronchoscopy to enable targeted removal of lesions ranging from suspected cancer to warty tracheal growths or laryngeal or vocal chord polyps or nodules. In such a case, the instrument would be used initially as a bronchoscope viewing through the blunt, enclosed distal end. Thereafter, targeting through the working area in conjunction with internalized fluid circulation would be used to remove multiple lesions quickly with concurrent cauterization of the base of the cut surface. In such a variant, an auxiliary port or additional soft and flexible tube would be included and protrude from the distal tip to vacuum any fluid that might exit or leak from the resection port during the actual cutting to avoid any flooding of the lung(s). Optionally or alternatively, a non-flammable, oxygen carrying fluid can be utilized as the infusion fluid if necessary or desired. Advantageously, use of the instant approach provides a speed advantage over laser ablation.

In the area of gastrointestinal surgery variants would be sized and dimensioned to allow for insertion, tissue biopsy and export with visual targeting. Here the shaft would primarily be a long and flexible fiberoptic shaft, as in the case of colonoscopic instruments generally, with only a small, rigid section near the distal end housing the working area and an intermediate reservoir piece intervening between the cutting member and the remainder of the flexible shaft.

In the area of cardiothoracic surgery variants could be used for biopsy of mediastinal cavity structures such as lymph nodes, or pericardial surfaces. Here the variant could incorporate, or be used in conjunction with, a specialized chest tube to allow for evaluation and diagnosis within the pleural space. In such applications, the shaft would be configured to be articulable or of a pre-specified shape and would be passed through a grommeted chest tube into the pleural space. Upon doing so, the shaft would be moved or articulated within the space to view and biopsy pleural lesion such as mesotheliomas, lymphomas or other lesions. Optionally, the tip can be configured to rotate axially to allow for initial drainage of a pyoma or malignant effusion via the chest tube with immediate rinsing, viewing and possible biopsy without recourse to standard thoracotomy incisions or multiple instrument insertion/removals.

In the area of orthopedic surgery variants can be sized and dimensioned to allow for passage into compartmental spaces or articular/joint spaces to allow for single incision joint space treatments.

In the area of maxillofacial surgery, variants would likely be configured to incorporate features applicable to the pulmonologic variant such as an optional integral inferior aspirator tube to clear mucous and rinsing fluid. Again, the shaft would be of appropriate dimensions and likely be at least slightly flexible along at least a portion of its length. Insertion into the nasal or sinus cavities, as with the above approaches, would occur while viewing through the blunt, enclosed distal end followed by specific targeting of, for example, polyps from the proximal side of the working area.

In all of the examples noted above, as well as any other non-enumerated surgical applications, owing to the tremendous variances among patients themselves, the numerous types and kinds of instances (as well as tissues) for which such variants might be used, it is contemplated that a "one-size fits all" approach may not be suitable. Advantageously, to accommodate such cases, variants incorporating the invention can be created in kit form so that, immediately prior to or during the surgical operation, the surgeon can have, for example, multiple shafts or other components available to them each of different configuration in terms of dimensions, resection ports, cutting members, etc. so that specialized, multiple different, or initial inspection-discovered atypical circumstances can be accommodated by, for example, last minute attachment of a particular shaft or changeover to a different shaft. While such cases could lead to more than one insertion, it is to be understood that such a disadvantage relative to single-insertion cases would still represent a marked improvement over conventional approaches.

Moreover, there may be certain instances where a surgeon may be unable to determine prior to beginning a surgical operation whether a variant incorporating the invention or a conventional approach can be used. Advantageously, in such cases, one or more variants can be kept "on-hand", the procedure can be initiated using a conventional approach and, should the need arise, the surgeon can quickly switch over to the variant if necessary or advantageous.

As a final note with respect to potential applications, although all of the above variants have been described with respect to typical human surgical applications, it is to be understood that the invention is applicable to use in animals generally (i.e. is by no means limited solely to use in humans) although human surgical applications are expected to be the primary use. Thus, it should be understood that implementations of the invention will have application in veterinary surgical operations as well.

Thus, it will be appreciated that, in many of the above variants, export of resected tissue occurs simply through fluid flow from the area of the distal tip/working region back towards the handle at the proximal end. Moreover, due to the unique configurations of many variants, tissue export can be augmented by using flow rates well in excess of what can be used with conventional instruments. This can be illustrated with reference to a intrauterine hysteroscopic procedure, bearing in mind that, increased flow rates may not be appropriate for all surgical procedures (i.e. where the tissue to be resected or the particular organ involved could be unacceptably damaged by such a flow).

When performing hysteroscopic surgery, surgeons typically use a 1.5% glycine solution. This glycine solution is hypotonic because it only has a 200-210 osmolarity, as compared with human serum which has better than roughly a 280 osmolarity. As a result, it is dangerous to absorb because it can cause hyponatremia, a low sodium condition which can result in coma, brain edema or, if such a condition occurs and is corrected too rapidly, central pontine dysmyelinosis. Thus, when performing conventional hysteroscopic operations, infusion pressures must be maintained during the entire operation and infusion pressure is intentionally limited in order to reduce and limit intravasation of the glycine solution. This limiting function is typically accomplished through use of an infusion pump operating at a setting derived from the average mean arterial pressure and abdominal weight of the patient in conjunction with the general experience of the surgeon. Generally, the setting is typically on the order of 75-80 mmHg (although the specific setting will vary depending on the mean arterial pressure and abdominal weight for a given patient).

With a conventional 8 mm Olympus resectoscope of 30 cm length similar to the resectoscope illustrated in U.S. Pat. No. 3,835,842 to Iglesias, a full open (i.e. maximum) infusion flow is about 1.2 liters per minute.

Based upon those parameters, it is expected that the same viscosity 1.5% glycine fluid used in a shaft according one variant of the invention configured with: a 12 mm external diameter, a 10 mm internal diameter, a length of 30 cm, a 2.7 mm diameter scope in its channel, a 5 mm diameter inflow tube, and one or more export pores with a total area equal to that of a single, circular export pore of 5 mm diameter, would be configured for a fluid infusion flow rate about equal to that of conventional instruments (i.e. about 1.2 liters per minute).

However, in the internal circulation mode (e.g. where resection and tissue export would occur), an increased fluid pressure or vacuum assist can readily be used to further advantage. Specifically, the internalized flow rate could readily be increased to double, triple or more of the maximum infusion flow rate, in this example, a rate that would be in excess of 4 liters per minute or more—a rate dramatically higher than would ever be used with conventional devices used in present surgical protocols. This is because, with conventional instruments, to the extent fluid is also drained by the instrument, the source for fluid is the body cavity itself. Thus, any removal rate that is greater than the inflow rate will tend to collapse the cavity and the addition of vacuum would only accelerate that collapse. In contrast, implementation variants such as disclosed herein would generally not deflate the cavity at all in the internal circulation mode because it is a substantially closed loop system (the possible exceptions being particular configurations where the window area is a hole that can not be blocked or where the resection port does not completely seal against the body cavity surface near an edge). However, even there, since bursts can be very short, cavity deflation risk is minimized notwithstanding the high fluid flow rate. In other words, with an internalized fluid circuit sourced by the inflow channel, a high flow rate can be used to export resected tissue without appreciably altering inflation of the cavity.

Of course, it is to be understood that, irrespective of the size of the inflow channel, the internal circulation rate will be limited by the smallest constriction through which the fluid will have to flow between the source and the infusion channel. Thus, the limitation will typically be based upon the size of the inflow tube and source line. In other words, larger flow rates would generally require a larger diameter inflow tube or source line or both. However, as will be appreciated, a larger diameter inflow tube can readily be provided up to, including, and through, one having of a cross sectional area that is equal to the cross sectional area of the infusion channel in the shaft. In addition, since it is expected that vacuum boosted flow rates will occur in bursts—not continuously—the use of a conventional 3 mm source line is not a problem if a sufficiently sized reservoir and inflow tube can be placed between the source line and the infusion channel.

Thus, it is expected that comparably sized variants can generally use internal circulation flow rates for tissue export (with or without vacuum assist) in excess of four times the rate of fluid infusion, thereby also providing reduced turbidity in the working area, more efficient cleaning of the scope or viewing apparatus end and/or reduced risk of a large piece of tissue becoming lodged within the shaft.

Although certain materials, features and configurations have been identified in connection with the above, they should not be considered literally the only materials, features or configurations that can be used. Particular materials, features and configurations will, to some extent, be determined by factors such as availability, cost, compatibility with the other components being used, compliance with regulations particular to surgical devices or manufacturing-related processes not pertinent to the inventive subject matter herein, only its particular implementation. Accordingly, it should be understood that those factors may result in a particular implementation having a configuration, features or materials that are not specifically described herein but should be considered as being suitable and within the contemplated scope, without specific itemization of all possible alternatives thereof.

For example, it may be desirable to use different cross sectional shapes for the shaft or its constituent channels for different applications. In other words, different configurations of ovoid, round or other geometric, non-geometric, symmetrical or non-symmetrical cross-sectional shapes may be desirable. Still further, the cross sectional shape may vary in different areas of the instrument. Similarly, different applications may make it desirable to use different orientations or groupings of channels due to specific fluid flow, tissue export, or other operational needs and/or to change parameters of the instrument itself to make it more suitable for a particular intended use, for example, to accommodate particular configurations or types of cutting members, deal with different organ particulars, increase or decrease shaft stiffness or maintain a given shaft stiffness or flexibility for different shaft diameters.

In some variants, tissue export can be augmented through use of a mechanical conveyor of some form or multiple elements acting in concert, for example, flexible millipede-like "graspers" or "pushers" between the working area and the location where the tissue exits the shaft or some form of "conveyor-belt"-like or large pitch helical screw arrangement which can be driven, for example, by the fluid flow in the shaft. Note however, that such an approach increases the mechanical complexity and consequently the likelihood of mechanical problems or failure and renders the instrument more difficult to clean and re-use. Nevertheless, such alternative approaches can be used from a pathology standpoint due to the increased size of the resected tissue relative to that obtained through current macerators or other resection devices used for similar purposes.

Still further, with respect to materials, any material that meets satisfies the intended use can be used in construction of the various elements, e.g. the shaft, cutting member, distal tip, handle, etc. For example, if the instrument will be reusable, in whole or part, in some applications, one or more of those components can be made from a metal, like stainless steel, or a polymer or polymer composite of suitable chemical or temperature resistance to enable it to withstand one or more re-sterilization cycles. One suitable example polymer is polyamideimide, also known as "PAI" or under the trade name Torlon® (a trademark of BP Amoco), which is commercially available form various suppliers including Quadrant Engineering Plastics Products of Reading, Pa. (www.quadrantepp.com). Another suitable example polymer is a polyethylene terephthalate thermoplastic polyester resin that is commercially available under the name Rynite® from E. I. du Pont de Nemours & Co. or one of its distributors.

In cases where the instrument or any of its components will be disposable after a single use, or may be re-usable a very limited number of times, less expensive materials that still meet the requirements for the particular component or action can be used, for example, low temperature plastics or materials that may only be suitable for a single or limited use because, for example, they can not stand up to re-sterilization or can only stand up to limited re-sterilization.

It should thus be understood that this description (including the figures) is only representative of some illustrative embodiments. For the convenience of the reader, the above description has focused on a representative sample of all possible embodiments, a sample that teaches the principles of the invention. The description has not attempted to exhaustively enumerate all possible variations. That alternate embodiments may not have been presented for a specific portion of the invention, or that further undescribed alternate embodiments may be available for a portion, is not to be considered a disclaimer of those alternate embodiments. One of ordinary skill will appreciate that many of those undescribed embodiments incorporate the same principles of the invention as claimed and others are equivalent.

What is claimed is:

1. A surgical instrument comprising:
   a shaft having a proximal end and a blunt, enclosed distal end, the blunt, enclosed distal end being optically transparent over at least a portion of its area, the shaft further comprising
   a longitudinally extending fluid infusion channel,
   a side wall having
      i) a resection port therein, near the distal end, defining an enclosed working area within which tissue can be resected, and
      ii) at least one fluid export pore,
   a longitudinally extending return channel coupling the working area to the proximal end dimensioned for passage of the resected tissue from the working area to the proximal end, and
   a movable fluid routing switch within the shaft and near the distal end which, when in a first position, will cause fluid traveling within the fluid infusion channel from the proximal end to the distal end to exit the shaft via the at least one fluid export pore and, when in a second position, will cause fluid traveling within the fluid infusion channel from the proximal end to the distal end to be routed within the shaft near the distal end so that it will pass through the working area and along the return channel towards the proximal end.

2. The surgical instrument of claim 1 wherein the movable fluid routing switch comprises a pivotable switch 3. The surgical instrument of claim 1 wherein the movable fluid routing switch comprises a reed switch.

4. The surgical instrument of claim 3 wherein the reed switch comprises at least one hole through which the fluid traveling within the fluid infusion channel can pass.

5. The surgical instrument of claim 1 further comprising:
a reflective surface proximate to the switch that is inclined relative to a longitudinal axis of the shaft.

6. The surgical instrument of claim 1 wherein the movable fluid routing switch is configured for actuation by one of a viewing instrument or a cutting member.

7. A surgical instrument comprising:
a shaft having a proximal end and a blunt, enclosed distal end, the shaft further comprising
a fluid infusion channel,
a return channel dimensioned for passage of resected tissue from a working area within the shaft near the distal end towards the proximal end,
at least one fluid export pore, and
a fluid routing switch within the shaft, near the distal end, which can selectively connect the fluid infusion channel to at least one of the at least one fluid export pore or the return channel.

8. The surgical instrument of claim 7 wherein the fluid routing switch comprises a pivotable switch 9. The surgical instrument of claim 7 wherein the fluid routing switch comprises a reed switch.

10. The surgical instrument of claim 7 further comprising:
a reflective surface near the fluid routing switch that is inclined relative to a longitudinal axis of the shaft.

11. A surgical instrument comprising:
a shaft having a proximal end, a working area defined by a port in a sidewall of the shaft, at least one fluid export port, and a blunt, enclosed distal end having an optically transparent portion;
at least two fluid conveying channels within the shaft; and
a switch within the shaft configured to selectively modify a connection
from being between one of the fluid conveying channels and the at least one fluid export port,
to being between the one of the fluid conveying channels and another of the fluid conveying channels.

12. A surgical instrument comprising:
a longitudinal shaft including
a) an enclosed, blunt distal tip;
b) an internal fluid flow path; and
c) an externalizable fluid flow path,
a working area, defined by an opening in a side of the longitudinal shaft, located within the internal fluid flow path, and
a switch, coupled to the internal fluid flow path and the externalizable fluid flow path which will control infusion fluid flow into the internal fluid flow path and the externalizable fluid flow path.

13. A resectoscope comprising:
the surgical instrument of one of claims 1, 7, 11 or 12 interconnected to
i) a handle having a tissue receiving cavity, and
ii) a cutting member.

14. A kit comprising:
the surgical instrument of one of claims 1, 7, 11 or 12 packaged in sterile form.

15. The kit of claim 14 further comprising:
a handle having a tissue receiving cavity therewithin.

16. The kit of claim 14 wherein the shaft is a single use shaft.

17. The kit of claim 14 further comprising:
a cutting member dimensioned for placement within the working area to effect tissue resection therewithin.

18. A neurosurgical instrument comprising:
a shaft, dimensioned for insertion through a cranial burr-hole, and having a proximal end and a blunt, enclosed distal end, the shaft further comprising
a fluid infusion channel,
a return channel dimensioned for drainage of fluid introduced into the cranium during insertion of the shaft and passage of resected tissue from a working area within the shaft near the distal end towards the proximal end,
at least one fluid export pore, and
a fluid routing switch within the shaft, near the distal end, which can selectively connect the fluid infusion channel to the at least one fluid export pore during incremental advancement of the instrument between the burr-hole and an area where tissue resection would occur or to the return channel to export the resected tissue from the working area.

19. A spinal microdiscectomy instrument comprising:
a shaft, dimensioned for insertion through a paraspinal incision, and having a proximal end and a blunt, enclosed distal end, the shaft further comprising
a fluid infusion channel,
a return channel dimensioned for passage of resected spinal disc tissue from a working area within the shaft near the distal end towards the proximal end,
at least one fluid export pore, and
a fluid routing switch within the shaft, near the distal end, which can selectively connect the fluid infusion channel to the at least one fluid export pore or to the return channel to export the resected spinal disc tissue from the working area.

20. An instrument for use in thoracic surgery comprising:
an articulable shaft, dimensioned for insertion through a chest tube into a pleural space, the shaft having a proximal end and a blunt, enclosed distal end, the shaft further comprising
a fluid infusion channel,
a return channel dimensioned for passage of resected tissue from a working area within the shaft near the distal end towards the proximal end,
at least one fluid export pore, and
a fluid routing switch within the shaft, near the distal end, which can selectively connect the fluid infusion channel to the at least one fluid export pore to allow tissue rinsing or to the return channel to export the resected tissue from the working area out of the pleural space.

21. An instrument for use in pulmonologic surgery comprising:
a shaft, dimensioned for insertion into one of a human laryngeal, tracheal or bronchial passage, the shaft having a proximal end and a blunt, enclosed distal end, the shaft further comprising
an auxiliary channel through which fluid can be moved from external to the shaft into the shaft by application of a vacuum to the auxiliary channel,
a fluid infusion channel,
a return channel dimensioned for passage of resected tissue from a working area within the shaft near the distal end towards the proximal end; and a fluid routing switch within the shaft, near the distal end, which can selectively connect the fluid infusion channel to the return channel to facilitate fluid driven export of the resected tissue from the working area.

22. An instrument for use in gastrointestinal surgery comprising:
   a shaft, dimensioned for insertion into a portion of the gastrointestinal tract of a human, the shaft having a proximal end and a blunt, enclosed distal end, the shaft further comprising
      a fluid infusion channel,
      a return channel dimensioned for passage of resected tissue from a working area within the shaft near the distal end towards the proximal end; and
      a fluid routing switch within the shaft, near the distal end, which can selectively connect the fluid infusion channel to the return channel to facilitate fluid driven export of the resected tissue from the working area.

23. A gynecological surgical instrument comprising:
   a shaft, dimensioned for insertion into the uterus via the cervix, and having a proximal end and a blunt, enclosed distal end, the shaft further comprising
      a fluid infusion channel,
      a return channel dimensioned for passage of resected tissue from a working area within the shaft near the distal end towards the proximal end,
      at least one fluid export pore, and
      a fluid routing switch within the shaft, near the distal end, which can be moved to connect the fluid infusion channel to the at least one fluid export pore to inflate the uterus and to connect the fluid infusion channel to the return channel to export the resected tissue from the working area.

24. A urological surgical instrument comprising:
   a shaft, dimensioned for insertion into the urethra, and having a proximal end and a blunt, enclosed distal end, the shaft further comprising
      a fluid infusion channel,
      a return channel dimensioned for passage of tissue, resected from within the urinary tract, from a working area within the shaft near the distal end towards the proximal end,
      at least one fluid export pore, and
      a fluid routing switch within the shaft, near the distal end, which can be moved to connect the fluid infusion channel to the at least one fluid export pore and to connect the fluid infusion channel to the return channel to form a fluid circuit within the shaft.

25. A surgical instrument comprising:
   a shaft, dimensioned for insertion into a facial cavity, and having a proximal end and a blunt, enclosed distal end, the shaft further comprising
      a fluid infusion channel,
      a return channel dimensioned for passage of tissue, resected from within the facial cavity, from a working area within the shaft near the distal end towards the proximal end,
      at least one fluid export pore, and
      a fluid routing switch within the shaft, near the distal end, which can be moved to connect the fluid infusion channel to the at least one fluid export pore to provide irrigation of the facial cavity and to connect the fluid infusion channel to the return channel to export the resected tissue from the working area.

26. An instrument for use in proctological surgery comprising:
   a shaft, dimensioned for insertion into a body via the anus, the shaft having a proximal end and a blunt, enclosed distal end, the shaft further comprising
      a fluid infusion channel,
      a return channel dimensioned for passage of resected tissue from a working area within the shaft near the distal end towards the proximal end; and
      a fluid routing switch within the shaft, near the distal end, which can selectively connect the fluid infusion channel to the return channel to facilitate fluid driven export of the resected tissue from the working area.

* * * * *